US008367801B2

(12) United States Patent
Hart

(10) Patent No.: US 8,367,801 B2
(45) Date of Patent: Feb. 5, 2013

(54) PROTEINACEOUS COMPOUNDS

(75) Inventor: John Ernest Hart, Tadley Hampshire (GB)

(73) Assignee: Endocrine Pharmaceuticals Limited, Tadley, Hampshire (GB)

( * ) Notice: Subject to any disclaimer, the term of this patent is extended or adjusted under 35 U.S.C. 154(b) by 178 days.

(21) Appl. No.: 12/812,503

(22) PCT Filed: Jan. 12, 2009

(86) PCT No.: PCT/GB2009/050021
§ 371 (c)(1),
(2), (4) Date: Jul. 12, 2010

(87) PCT Pub. No.: WO2009/087424
PCT Pub. Date: Jul. 16, 2009

(65) Prior Publication Data
US 2010/0292438 A1 Nov. 18, 2010

(30) Foreign Application Priority Data

Jan. 10, 2008 (GB) .................................. 0800373.3
Jan. 11, 2008 (GB) .................................. 0800502.7

(51) Int. Cl.
*A61K 38/04* (2006.01)
*C07K 5/00* (2006.01)
*C07K 7/00* (2006.01)
*C07K 16/00* (2006.01)
*C07K 17/00* (2006.01)
(52) U.S. Cl. .................... 530/327; 530/329; 530/330
(58) Field of Classification Search .................. None
See application file for complete search history.

(56) References Cited

U.S. PATENT DOCUMENTS 6,962,974 B1 * 11/2005 Kalluri ........................... 530/350
2007/0020625 A1 * 1/2007 Duchaud et al. .................. 435/6

FOREIGN PATENT DOCUMENTS

| EP | 1262 562 A2 | * | 4/2002 |
| WO | WO 94/20127 | * | 9/1994 |
| WO | 00/32208 A2 | | 6/2000 |
| WO | WO 01/92523 A2 | * | 12/2001 |

OTHER PUBLICATIONS

Omura et al. Genome sequence of an industrial microorganism *Streptomyces avermitilis*: Deducing the ability of producing secondary metabolites. PNAS, 2001. vol. 98, No. 21, pp. 12215-12220.*
Fujisawa. Immunohistochemical Localization and Ca2+-Dependent Release of Mytilus Inhibitory Peptides in the ABRM of *Mytilus edulis*. Zoological Science, 1996. vol. 13, No. 6, pp. 795-801.*
PCT/ISA/210—International Search Report for corresponding International Application No. PCT/GB2009/050021, mailed Nov. 2, 2009.
PCT/ISA/237—Written Opinion of International Searching Authority for corresponding International Application No. PCT/GB2009/050021, mailed Nov. 2, 2009.
STN Database Registry—Database Accession No. 727488-83-7, dated Aug. 16, 2004.
Hart et al., "Pituitary-related weight changes affecting the liver, uterus and adrenal glands of rats treated with hexoestrol and clomiphene in high doses," *Toxicology*, vol. 61, No. 2, Apr. 17, 1990, pp. 185-194.
Haylor et al , "Inhibition of compensatory renal growth by the N-terminus of a sheep-derived peptide," *Regulatory Peptides*, vol. 152, No. 1-3, Jan. 8, 2009, pp. 48-53.
Davies et al., "Fecundity and lifespan manipulations in *Caenorhabditis elegans* using exogenous peptides," *Nematology*, vol. 10, No. Part 1, 2008, pp. 103-112.

* cited by examiner

*Primary Examiner* — Marcela M Cordero Garcia
(74) *Attorney, Agent, or Firm* — Heslin Rothenberg Farley & Mesiti P.C.; Andrew K. Gonsalves

(57) ABSTRACT

A purified novel peptide micrin and its fragments are disclosed. The molecule has hormonal functions and has wide-ranging biological effects. Several uses are disclosed including its therapeutic potential in tissue reduction, tumour suppression, infertility and senescence. A micrin-recognising antibody and the micrin gene are also disclosed.

7 Claims, 9 Drawing Sheets

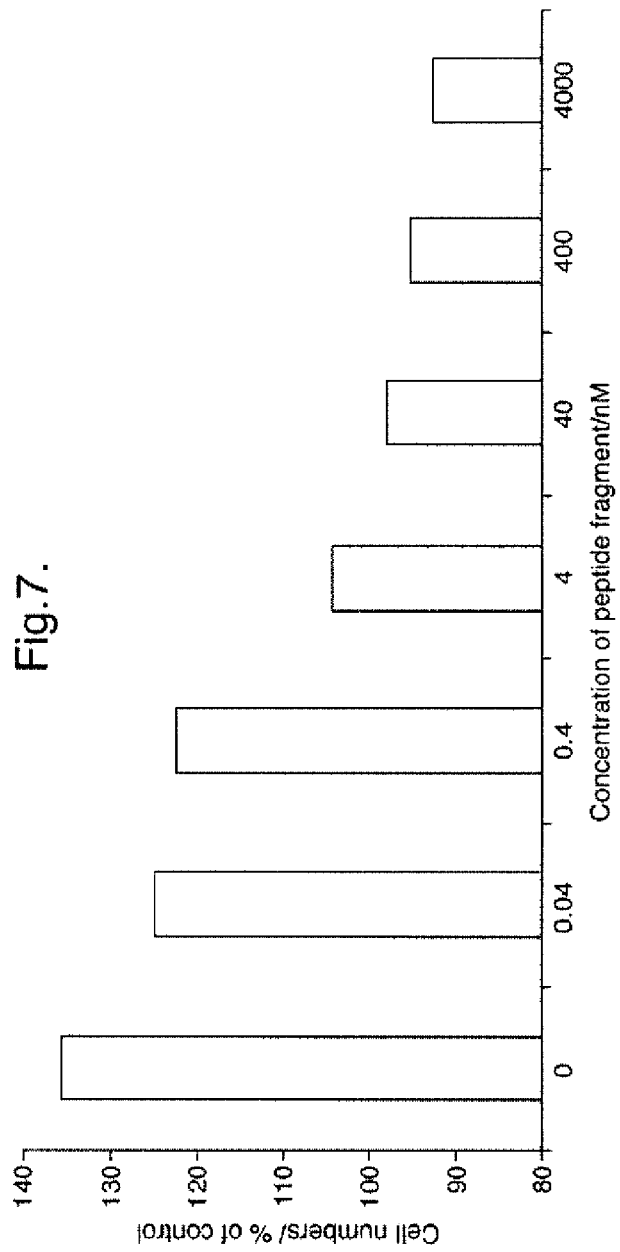

Figure 8

```
ggcacctacc ttgtcagctt cactctgttc tgggagggcc aggtctccct
gtctatcctg ctcatgcacc ccagtgaagg ggtgtcagct ctctggagag
caaggaacca gggttacgac agaatcatct tctcaggcca ttttgtcagt
ggcgcttcca ggtccacacc gattgtgccc tggttctaaa ttcaagtgtc
gagctatgtc agtatctgga tgcccaggac caagaagctt tctactgtgt
gaagcctcca aatgtgccct gtgcggccat cacccacatg cattccaaga
acaaggacat ttcttatctt agccagcagg aaaggagcct ctttgaaagg
tcaaatatag ctgtggagat tatgggaaaa tccaacgtga ttagtgtctc
caaatgcaac aaagccgtcc cggtgaagaa gaaatgcaag tttgggatgg
catctgcaat ccctactggg catgtctgga aaaacacgtg gaatccggcc
tcctgcagtc tggctccaat caaaatgaaa gactgcctga gaggaaaact
cgtccatcta atgggtgatt ccacaatgcg ccagtggatg gagtacttca
aaagcaaaat caacacgctg aggccggtgg acctccacga gactggaagg
ctgcagcacc aacttgccgt ggacttggat gagaaaatca acatccagtg
gcagaaacat ggcttccctc taatcgggtc attggtgtac tctgtcaaag
agatagagaa cactgcacgg ataattgaca gaatcggagg agagaaaaac
acagtcattg tcttttctct gggccagcat ttcagacctt ttcccattga
tgtttttatc cgaagggccc tcagtgttc
```

```
GTYLVSFTLF WEGQVSLSIL LMHPSEGVSA LWRARNQGYD RIIFSGHFVS
GASQVHTDCA LVLNSSVELC QYLDAQDQEA FYCVKPPNVP CAAITHMHSK
NKDISYLSQQ ERSLFERSNI AVEIMGKSNV ISVSKCNKAV PVKKKCKFGM
ASAIPTGHVW KNTWNPASCS LAPIKMKDCL RGKLVHLMGD STMRQWMEYF
KSKINTLRPV DLHETGRLQH QLAVDLDEKI NIQWQKHGFP LIGSLVYSVK
EIENTARIID RIGGEKNTVI VFSLGQHFRP FPIDVFIRRA LSV
```

Figure 9

```
atgaaaatgatggccagtcgtaagtcactgtgggtgctg
 M  K  M  M  A  S  R  K  S  L  W  V  L
ctgtttatagtgatcttctggatctcttttaccgttttcagaaacccgtgaagctatgg
 L  F  I  V  I  F  W  I  S  F  T  V  F  R  N  P  V  K  L  W
gctgtgtttaagctgcctgcatccttcaatcaatgggacttgatcatgaaatcctcatgc
 A  V  F  K  L  P  A  S  F  N  Q  W  D  L  I  M  K  S  S  C
cctaaagtgcctctcaatccatcagtttcaccaacagagacagagctgagaatcagggag
 P  K  V  P  L  N  P  S  V  S  P  T  E  T  E  L  R  I  R  E
atcctagagaaactaaacaaacagatccctcccagacccttcgcccacctcaacaacacc
 I  L  E  K  L  N  K  Q  I  P  P  R  P  F  A  H  L  N  N  T
acaagtgctacacacagcatagccaccatcctcaaccctcaagatacatactgtgtaggg
 T  S  A  T  H  S  I  A  T  I  L  N  P  Q  D  T  Y  C  V  G
gaccagctggacatcctggtagaggctagagaccacctaagaaacaggaaagggtatggt
 D  Q  L  D  I  L  V  E  A  R  D  H  L  R  N  R  K  G  Y  G
ggggacttcctgagggccaggatgtcttctccagccctgaaggcaggcgcttctggaaaa
 G  D  F  L  R  A  R  M  S  S  P  A  L  K  A  G  A  S  G  K
gtgacagacttcaacaatggcacctaccttgtcagcttcactctgttctgggagggccag
 V  T  D  F  N  N  G  T  Y  L  V  S  F  T  L  F  W  E  G  Q
gtctccctgtctatcctgctcatgcaccccagtgaaggggtgtcagctctctggagagca
 V  S  L  S  I  L  L  M  H  P  S  E  G  V  S  A  L  W  R  A
aggaaccagggttacgacagaatcatcttctcaggccattttgtcagtggcgcttctcag
 R  N  Q  G  Y  D  R  I  I  F  S  G  H  F  V  S  G  A  S  Q
gtccacaccgattgtgccctggttctaaattcaagtgtcgagctatgtcagtatctggat
 V  H  T  D  C  A  L  V  L  N  S  S  V  E  L  C  Q  Y  L  D
gcccaggaccaagaagctttctactgtgtgaagcctccaaatgtgccctgtgcggccatc
 A  Q  D  Q  E  A  F  Y  C  V  K  P  P  N  V  P  C  A  A  I
acccacatgcattccaagaacaaggacatttcttatcttagccagcaggaaaggagcctc
 T  H  M  H  S  K  N  K  D  I  S  Y  L  S  Q  Q  E  R  S  L
tttgaaaggtcaaatatagctgtggagattatgggaaaatccaacgtgattagtgtctcc
 F  E  R  S  N  I  A  V  E  I  M  G  K  S  N  V  I  S  V  S
aaatgcaacaaagccgtcccggtgaagaagaaatgcaagtttgggatggcatctgcaatc
 K  C  N  K  A  V  P  V  K  K  K  C  K  F  G  M  A  S  A  I
cctactgggcatgtctggaaaaacacgtggaatccggcctcctgcagtctggctccaatc
 P  T  G  H  V  W  K  N  T  W  N  P  A  S  C  S  L  A  P  I
aaaatgaaagactgcctgagaggaaaactcgtccatctaatgggtgattccacaatgcgc
 K  M  K  D  C  L  R  G  K  L  V  H  L  M  G  D  S  T  M  R
cagtggatggagtacttcaaaagcaaaatcaacacgctgaggccggtggacctccacgag
 Q  W  M  E  Y  F  K  S  K  I  N  T  L  R  P  V  D  L  H  E
actggaaggctgcagcaccaacttgccgtggacttggatgagaaaatcaacatccagtgg
 T  G  R  L  Q  H  Q  L  A  V  D  L  D  E  K  I  N  I  Q  W
cagaaacatggcttccctctaatcgggtcattggtgtactctgtcaaagagatagagaac
 Q  K  H  G  F  P  L  I  G  S  L  V  Y  S  V  K  E  I  E  N
actgcacggataattgacagaatcggaggagagaaaaacacagtcattgtcttttctctg
 T  A  R  I  I  D  R  I  G  G  E  K  N  T  V  I  V  F  S  L
ggccagcatttcagaccttttcccattgatgtttttatccgaagggccctcagtgttcac
 G  Q  H  F  R  P  F  P  I  D  V  F  I  R  R  A  L  S  V  H
agagctcttcagcgtcttctcctgagaagcccggacaccctggtggtcctcaaaacagaa
 R  A  L  Q  R  L  L  L  R  S  P  D  T  L  V  V  L  K  T  E
aacaccagggagttgaataacgacatggagaggtttagtgacttccacggttacacccag
 N  T  R  E  L  N  N  D  M  E  R  F  S  D  F  H  G  Y  T  Q
tatcttgccttaaagaatatcttccaggatctccgtgtgggtgtcattgatgcctgggat
 Y  L  A  L  K  N  I  F  Q  D  L  R  V  G  V  I  D  A  W  D
atgacagttgcatatggcacaaacgatgtccatccaccagaggaggtagttagaagtgaa
 M  T  V  A  Y  G  T  N  D  V  H  P  P  E  E  V  V  R  S  E
attaatatattcttaaactatatttgctagcaaacacataactttgaaagtcgctcgttg
 I  N  I  F  L  N  Y  I  C
```

PROTEINACEOUS COMPOUNDS

CROSS REFERENCE TO RELATED APPLICATIONS

This application is a U.S. National Phase filing under 35 U.S.C. §371 of International Application No. PCT/GB2009/050021, filed Jan. 12, 2009, and published as WO 2009/087424 on Jul. 16, 2009, which claims priority to Great Britain Patent Application No. GB 0800373.3, filed Jan. 10, 2008, and Great Britain Patent Application No. 0800502.7, filed Jan. 11, 2008, the entire disclosures of which are incorporated herein by reference.

FIELD OF THE INVENTION

The present invention relates to a physiologically active peptide and physiologically active parts thereof. In particular, the invention relates to a physiologically active peptide or parts thereof possessing an apparent hormonal function, isolated amino acid sequences thereof and isolated nucleic acid sequences therefor, uses thereof such as prophylactic and therapeutic uses in the treatment of disease, and compositions comprising at least one peptide of the invention. Peptides of the invention have wide applicability in the control of the growth, size, shape, integrity, reproduction and other characteristics of cells, groups of cells, tissues, organs, structures and whole organisms, such as in the reduction in growth of tumours and metastases, in infertility and in stem cell production, usage and control.

BACKGROUND OF THE INVENTION

Organ differential-growth models indicate that control of organ size occurs at the level of the entire tissue volume; that is, no single factor such as cell size or the number of cells within the organ is responsible for size of the organ. How organ mass is sensed is not known. The system of control is complex, as well as robust and stable towards changes in individual factors (Desplan, C. and Lecuit, T., Nature, 422, 123-124, 2003).

An integrated picture has yet to emerge of the totality of controls on tissue and internal organ size, either during development or adulthood. Known molecular influences tend to be upregulatory (i.e. stimulatory, such as growth hormone and the sex steroids), stimulatory or inhibitory depending on the situation (e.g. TGFβ), or specifically inhibitory (e.g. locally produced myostatin on muscle, or Noggin, which counters the growth factor bone morphogenetic protein 7), rather than generally inhibitory, as in the present invention. Further examples of intercellular signalling molecules which might play a role in the control of organ size and form include classical hormones such as insulin and prolactin; effectors such as IGF1 and 2, TGFα, epidermal growth factor (EGF), vascular endothelial growth factor (VEGF) and fibroblast growth factor (FGF); and morphogens involved in differentiation and patterning such as Wnt, Notch and Hedgehogs.

Circulating hormone levels can control tissue and organ size directly, as in the case of upregulation of the size of the prostate gland by androgens. Some agents influence growth indirectly on a 'global' scale in the body, by exerting an effect on central hormonal growth control in the hypothalamus and pituitary. Estrogen, while also having local effects, is an example of a hormone that exerts control on growth and size in this way. Of particular interest is when the decision point is reached to reproduce rather than continue growing.

In WO 00/32208 impure preparations of sheep ovarian venous plasma were used to show that fractions collected in the 10-30 kDa nominal molecular weight range contained a material which reduced organ mass in adult rats. This was the first time it was shown that a general inhibitor of organ mass existed. The unknown active entity in the material was named 'micrin'. That document provided no information on the chemical nature of micrin.

An object of the present invention is to overcome deficiencies of the prior art. This and other objects will become apparent from the following description.

SUMMARY OF THE INVENTION

The invention provides a physiologically active peptide and/or parts thereof in essentially pure form for the first time. For the purposes of the present invention peptides of the invention and their derivatives as described herein are referred to as 'micrins' or 'micrin' and possess micrin functionality as herein described. The inventor has shown that micrin is a polypeptide and has a molecular weight between 7000 and 8000 Da, of approximately 7500 Da, and an isoelectric point of pH 6.5. The invention also provides peptide fragments of micrin comprising one or more physiologically active motifs therein, such as a fragment with a molecular weight of between 1400 Da and 2500 Da.

According to a first aspect of the present invention there is provided an isolated polypeptide comprising a 5 mer of Formula (I):

$$1\text{-}2\text{-}P\text{-}3\text{-}4 \qquad (I)$$

wherein
1 is independently selected from amino acids S, D, L, I and M;
2 is independently selected from amino acids S, Q, E, K, L and T;
3 is independently selected from amino acids A, V, L, F, G and E;
4 is independently selected from L, H, M, T and F; and
P is a proline residue Preferably, an isolated polypeptide of the invention comprising a 5 amino acid long sequence of Formula (I) further comprises an additional sixth amino acid, forming a 6 mer of Formula (II):

$$1\text{-}2\text{-}P\text{-}3\text{-}4\text{-}5 \qquad (II)$$

wherein 1, 2, 3, and 4, are as defined for Formula (I), and 5 is independently selected from amino acids V, T and G.

Preferably, according to a further aspect of the present invention there is provided an isolated polypeptide that comprises an amino acid sequence according to Formula (III):

$$1\text{-}2\text{-}P\text{-}3\ 4\text{-}5\text{-}6\text{-}7\text{-}K\text{-}8\text{-}F\ N\ 9\text{-}10 \qquad (III)$$

wherein
1 is independently selected from S, D, L, I, and M;
2 is independently selected from S, Q, E, K, L and T;
3 is independently selected from A, V, L, F, G and E;
4 is T;
5 is independently selected from V, T, G and Y;
6 is independently selected from K and W;
7 is independently selected from V and I;
8 is independently selected from E and K;
9 is independently selected from N and A; and
10 is independently selected from 1 and V.

Preferred sequences of isolated polypeptides of the invention include sequences of Formula (III) wherein
1 is independently selected from S, D and M;
2 is independently selected from K and L;

3 is independently selected from L, F, and G;
5 is G;
6 is independently selected from K and W;
7 is V;
8 is independently selected from E and K;
9 is N; and
10 is I.

More preferred sequences of polypeptides of the invention include sequences of Formula (III) wherein
1 is independently selected from S, D and M;
2 is K;
3 is independently selected from L and F;
5 is G;
6 is K;
7 is V;
8 is E;
9 is N; and
10 is I.

Most preferred sequences of Formula (III) conform to SEQ ID No.1:

```
1KPLTGKVKEFNNI          (SEQ ID NO. 1)
``` wherein
1 is independently selected from S, D, and M.

SEQ ID NO: 1 is comprised in the full length micrin peptide. Preferably, the isolated amino acid sequence of Formula (I) includes a stabilising functionality, such as K G F X V I (SEQ ID NO. 6) as found in the sequence designated as SEQ ID NO. 2:

```
1KPLTGKVKEFNNIKGFXVI    (SEQ ID NO. 2)
``` wherein 1 is either S, D or M; and
'X' represents any amino acid residue.

Naturally, the skilled addressee will appreciate that the 6-mer motif located at the N-terminus may be separated from the FNN-containing motif by a spacer of up to 20 amino acids, usually up to 10 amino acids and preferably from about, 4, 6, 8 or 9 amino acids, for example 4 amino acids. Accordingly, there is provided an isolated micrin polypeptide of the invention comprising an amino acid sequence of Formula (IV):

$$1\text{-}2\text{-}P\text{-}3\text{-}4\text{-}5(Z)_n\text{-}11\text{-}12\text{-}N\text{-}13 \quad (IV)$$

wherein
1 is independently selected from amino acids S, D, L, I and M;
2 is independently selected from amino acids S, Q, E, K, L and T;
3 is independently selected from amino acids A, V, L, F, G and E;
4 is independently selected from L, H, M, T and F;
5 is independently selected from V, T and G;
P is a proline residue
Z is a sequence of amino acid residues;
11 is independently selected from F and Y;
12 is independently selected from N and Q;
13 is independently selected from 1 and G; and
n is 0 or a whole integer selected from 1 to 20.

Preferably n is 0 or a whole integer selected from 1 to 10, more preferably n is selected from 0, 4, 6, 8 or 9; Z is a linker sequence of amino acid residues and does not constitute a physiologically active motif that is indicative of a physiologically functional micrin polypeptide of the invention; 11 is F; 12 is N, and 13 is I or G. Preferably, the portion of Formula (IV) that is –11-12-N-13 is selected from FNNI (SEQ ID NO. 4) and FNNG (SEQ ID NO. 5).

In a further aspect of the invention, there is provided an isolated amino acid sequence of Formula (V):

$$11\text{-}12\text{-}N\text{-}13 \quad (V)$$

wherein
11 is independently selected from Y and F;
12 is independently selected from N and Q; and
13 is independently selected from G and I.

Preferably, the isolated amino acid sequence of Formula (V) is FNNI or FNNG.

In a further aspect of the invention, there is provided isolated physiologically active amino acid motifs of the invention that conform with the definitions as provided independently herein of Formula (I), Formula (II), Formula (III), Formula (IV) and Formula (V) as herein provided.

It will be appreciated that the invention preferably, includes any peptide sequence having substantial homology to the amino acid sequence SEQ ID NO. 1 and/or SEQ ID NO. 2. The level of homology should be at least 50%, preferably at least 70% and more preferably greater than 90%, such as 91%, 92%, 93%, 94%, 95%, 96%, 97%, 98%, or 99%. The full length polypeptide or a functional fragment thereof as described herein, may additionally include a signal sequence as commonly employed in the art. It will be further appreciated that the invention includes any peptide or variants thereof comprising substantially the same biological or physiological activity as the peptides of the invention. Typically, polypeptides with more than about 50%, 55% or 65% identity preferably at least 80%, more preferably at least 90%, 91%, 92%, 93%, 94%, 95%, 96%, 97%, 98% or 99% such as 95%, 97% or 99% identity, with the amino acid sequence of SEQ ID NO: 1 or SEQ ID NO: 2, are considered variants of the peptides of the invention. Such variants may include allelic variants, deletion variants, or variants comprising modifications or additions of single amino acids or groups of amino acids to the peptide sequence, as long as the peptide sequence of the invention maintains the basic functionality of a micrin peptide of the invention.

Micrin may exist as a number of isoforms which comprise a family of molecules. Members of this micrin family of molecules may differ in primary amino acid sequence by virtue of different post-translational modifications of one or more amino acids within the sequence. Any reference to micrin herein includes reference to any member of the micrin family.

Amino acid substitutions may be made to the polypeptide, peptide fragments and/or active motifs therein. The modified moieties generally retain the physiological activity of a micrin peptide of the invention. Conservative substitutions may be made, for example according to the following Table 1.

TABLE 1

| Amino acid substitution: amino acids in the same block in the second column and preferably in the same line in the third column may be substituted for each other. | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Polypeptides of the invention may also be chemically modified, e.g. post-translationally. For example, they may be glycosylated or comprise modified amino acid residues. They may be modified by the addition of histidine residues to assist their purification or by the addition of a signal sequence to promote insertion into the cell membrane. It may be desirable to provide the peptides or proteins in a form suitable for attachment to a solid support. The proteins or peptides may thus be modified to enhance their binding to a solid support for example by the addition of a cysteine residue. Such modified polypeptides fall within the scope of the term 'polypeptide' of the invention.

As alluded to herein, polypeptides of the invention may be provided in a substantially isolated form. It will be understood that such polypeptides may be mixed with carriers or diluents, thus forming compositions comprising micrin or micrin polypeptides. Such carriers, diluents and excipients and the like should be ones which will not substantially interfere with the physiological functional integrity of the micrin polypeptide or micrin polypeptides of the invention. The polypeptide of the invention may also be in a substantially purified form, in which case it will generally comprise the polypeptide in a preparation in which more than 50%, e.g. more than 80%, 85%, 90%, 91%, 92%, 93%, 94%, 95%, 96%, 97%, 98% or 99%, such as 95% or 99%, by weight of the polypeptide in the preparation is a polypeptide of the invention.

According to another aspect of the present invention, there is provided an isolated nucleotide sequence that encodes a micrin peptide of the invention. Suitable nucleotide sequences of the invention include the nucleotide sequence designated as SEQ ID NO: 16. SEQ ID NO: 16 encodes a portion of the amino acid sequences making up SEQ ID NO: 1 and/or 2.

The invention includes any isolated polynucleic acid sequence or nucleotide sequence that includes a portion thereof that shows substantial homology to SEQ ID NO: 16. Preferably, the isolated polynucleic acid sequence conforms to a micrin polynucleic acid sequence of the invention as described herein. The level of homology should be at least 50%, preferably at least 70%, and more preferably greater than 90%. It is well known that members of gene families which share functional motifs may have low overall homology. In a further embodiment of the invention the overall level of homology is less than 50% at the amino acid level (i.e. when the nucleotide sequence is translated in silico to an amino acid sequence), whilst the level of homology at the site of one or more functional motifs is greater than 50% at the amino acid level.

In particular the invention relates to polynucleotides comprising (a) the coding sequence of SEQ ID NO: 16 or a complementary sequence thereto; (b) a sequence which hybridises under stringent conditions to the sequences defined in (a); (c) a sequence which is degenerate as a result of the genetic code to a sequence as defined in (a) or (b); (d) a sequence having at least 60% identity to sequences defined in (a), (b) or (c); and (e) a fragment of any of the sequences under (a), (b), (c) or (d) that are able to give rise to physiologically functional peptide sequences of the invention.

Typically the isolated polynucleotide is comprised of DNA or RNA. The polynucleotides may be single or double stranded, and may include within them synthetic or modified nucleotides. Modified nucleotides may include those modified on the phosphate moiety, such as phosphorothioate nucleotides; on the base moiety, such as fluorescent or haptenic groups attached to the base at suitable positions known to those skilled in the art; or on the sugar moiety, such as modifications at the 2'-carbon. Examples of modified nucleotides include monomethyl, dimethyl and trimethyl guanosine; acetyl cytidine; deoxycytidine; and methyl adenosine.

The polynucleotides of the invention can be used in the production of polypeptides of the invention, which may take place in vitro, in vivo or ex vivo. The polynucleotides may be used as therapeutic agents in their own right or may be involved in recombinant protein synthesis.

The polynucleotides of the invention may be used as a primer, e.g. a PCR primer, a primer for an alternative amplification reaction, a probe e.g. labelled with a revealing label by conventional means using radioactive or non-radioactive labels, or the polynucleotides may be cloned into vectors. Suitable labels include radioisotopes such as $^{32}P$ or $^{35}S$, enzyme labels, or other protein labels such as biotin.

According to another aspect of the invention there is provided a method for detecting or sequencing micrin in a sample using the polynucleotides or primers of the invention or fragments thereof, labelled or unlabelled.

Such tests for detection generally comprise bringing a sample containing DNA or RNA into contact with a probe comprising a polynucleotide or primer of the invention under hybridising conditions and detecting any duplex formed between the probe and nucleic acid in the sample. Such detection may be achieved using techniques such as PCR or by immobilizing the probe on a solid support, removing nucleic acid in the sample which is not hybridised to the probe, and then detecting nucleic acid which has hybridised to the probe. Alternatively, the sample nucleic acid may be immobilized on a solid support, and the amount of probe bound to such a support can be detected.

The probes of the invention may conveniently be packaged in the form of a test kit in a suitable container. In such a kit, the probe may be bound to a solid support where the assay format for which the kit is designed requires such binding. The kit may also contain suitable reagents for treating the sample to be probed, hybridising the probe to nucleic acid in the sample, control reagents, instructions, and the like.

According to a further aspect of the invention there is provided a recombinant replicable vector comprising the polynucleotide of the invention. The vector may be used to replicate the nucleic acid in a compatible host cell. Therefore, polynucleotides of the invention may be made by introducing a polynucleotide of the invention into a replicable vector, introducing the vector into a compatible host cell and growing the host cell under conditions which bring about replication of the vector.

Preferably the vector is an expression vector comprising a nucleic acid sequence that encodes a polypeptide of the invention. Such expression vectors are routinely constructed in the art of molecular biology and may for example involve the use of plasmid DNA and appropriate initiators, promoters, enhancers and other elements, which may be necessary, and which are positioned in the correct orientation, in order to allow for protein expression.

Polynucleotides according to the invention may also be inserted into a vector in an antisense orientation in order to provide for the production of antisense RNA. Antisense RNA or other antisense polynucleotides, such as siRNAs or microRNAs relating to nucleic acid sequences coding for physiologically active motifs of micrin as described herein, may also be produced by synthetic means. Thus, as a further aspect of the invention there is provided an siRNA sequence that codes for a physiologically active amino acid motif of a micrin polypeptide. Suitable micrin motifs are as described and defined herein and include inter alia FNNI and FNNG, Such antisense polynucleotides may be used as test compounds in the assays of the invention or may be useful in a method of treatment of the human or animal body by therapy in both sense and anti-sense orientation depending on end purpose.

The vectors may be, for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a resistance gene for a fungal vector.

The vector may further include sequences flanking the polynucleotide, giving rise to polynucleotides which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide into the host genome. Replication-defective adenovirus vectors by contrast remain episomal and therefore allow transient expression.

Vectors may be used in vitro, for example for the production of DNA or RNA or used to transfect or transform a host cell, for example, a mammalian host cell. The vectors may also be adapted to be used in vivo, for example in a method of gene therapy or nucleic acid immunisation.

According to a further aspect of the present invention there is provided a process for purifying a micrin peptide from a biological sample that comprises
 a) passing plasma through an ultrafiltration membrane forming a filtrate;
 b) concentrating the filtrate using a filter with a weight cut-off of 3000 Da and obtaining a precipitate;
 c) resuspending the precipitate in a fluid; and
 d) re-forming a precipitate and separating it out.

Preferably the purification process further includes a gel electrophoresis step.

The described purification process may be used to separate micrin from other biological materials, such as serum, ovarian follicular fluid, urine, milk, cerebrospinal fluid, seminal fluid, and extracts of mammalian organs.

It will be appreciated that fragments of the full length micrin polypeptide, which may include the peptide sequence with the desired biological activity, or the full length micrin molecule, may be produced independently of the above purification technique by organic synthesis methods known to a person skilled in the art, for example using solid phase or solution phase synthesis. Alternatively, they may be produced by recombinant DNA techniques (using oligonucleotide sequences relating to the amino acid sequences) to express the peptides in various hosts, for example bacteria, yeast, mammalian cells, hens' eggs, insect cells or transgenic animals. Other techniques using promoters to over-express the native micrin gene or cDNAs coding for micrin peptides may also be used. The fragments of micrin as well as the whole micrin molecule prepared in these ways are a further aspect of the invention.

Further, analogues of micrin or analogues of peptides comprising amino acid sequences of Formula (I), and preferably of SEQ ID NO: 1 or SEQ ID NO: 2 may be prepared using standard techniques. Such analogues may vary by one or more amino acids (natural amino acids and/or synthesised amino acid analogues) and may alter the activity, stability, bioavailability or other characteristics of the molecule in vivo or in vitro. Modification of the amino acids with side chains using chemical or enzymatic methods may result in moieties with improved activity, stability, bioavailability or other characteristics. Such analogues and modifications are a further aspect of the invention.

According to a still further aspect of the invention, there is provided a polyclonal or a monoclonal antibody to a synthetic amino acid sequence of Formula (I), (II), (III), (IV) or (V) such as polyclonal and monoclonal antibodies to an amino acid sequence corresponding to SEQ ID NO. 1 and/or SEQ ID NO. 2 that are capable of binding to epitopes located therein. Such antibodies may be used for the extraction of the micrin polypeptide from natural sources via immunoaffinity chromatography (or related methods); for the quantification or localisation of micrin in biological samples (fluids, tissues etc.); and for the provision of micrin-free cell culture media. The antibodies may also then be used to block the inhibitory action of micrin or micrins or an active fragment or fragments thereof either in a therapeutic context, a prophylactic context or in vitro for research or diagnostic purposes. Non-human animal models may be created where the prevention of tissue overgrowth is blocked by the micrin antibody, for example, in cancer studies.

For the purposes of this invention, the term 'antibody', whether monoclonal or polyclonal, unless specified to the contrary, includes fragments which bind a polypeptide of the invention. Such fragments include Fv, F(ab') and $F(ab')_2$ fragments, as well as single chain antibodies. Furthermore, the antibodies and fragment thereof may be chimeric antibodies, CDR-grafted antibodies or humanised antibodies.

According to another aspect of the present invention there is provided an ELISA assay for the detection and measurement of micrin using the antibodies described herein. The assay may be used for the monitoring of therapeutic treatment with micrin, monitoring levels of micrin in normal or disease states, or in drug discovery and other types of research.

According to a further aspect of the invention there is provided a pharmaceutical composition comprising a micrin polypeptide comprising a peptide sequence according to Formula (I), and, preferably, a micrin polypeptide comprising SEQ ID NO: 1 and/or SEQ ID NO: 2 and a pharmaceutically acceptable diluent, carrier or excipient. In a further aspect, the pharmaceutical composition may comprise an agonist of micrin or a micrin antagonist. Further, the pharmaceutical composition may comprise a modified micrin peptide or analogues of micrin. The pharmaceutical preparations may be used for the prophylaxis and treatment of diseases. The compositions may be administered by enteral or parenteral routes such as oral, buccal, anal, pulmonary, intravenous, intra-arterial, intramuscular, intraperitoneal, topical, in a medicated tampon, by suppository or local delivery by implanted osmotic pumps or other appropriate administration routes, or by other methods used for the administration of peptides such as implants, stents and prostheses. The proteins or peptides of the invention may be formulated as neutral or salt forms. Pharmaceutically acceptable salts include the acid addition salts (formed with free amino groups of the peptide) which are formed with inorganic acids such as, for example, hydrochloric or phosphoric acids, or such organic acids such as acetic, oxalic, tartaric and maleic acid. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine. The peptides are administered in a manner compatible with the dosage formulation and in such an amount as will be prophylactically and/or therapeutically effective.

In another aspect, the pharmaceutical composition may comprise the micrin gene or an oligonucleotide sequence comprising SEQ ID NO: 16 or a functionally equivalent variant of the micrin gene or cDNA for micrin or a micrin-associated gene or cDNA sequence. Such pharmaceutical compositions may incorporate oligonucleotide sequences relating to the various micrin peptide forms, and administered as herein described or by liposomal, viral, plasmid or phage vector, or other gene therapy approaches known in the art. These pharmaceutical preparations may also be included in or on implantable medical devices, such as stents.

In a further aspect, the pharmaceutical composition may comprise an antibody to a full length micrin of the invention or an antibody to a fragment of a full length micrin of the invention or an antibody to a micrin-like polypeptide sequence according to Formula (I), such as SEQ ID NO: 1 or SEQ ID NO: 2.

According to a further aspect of the invention there is provided the use of a micrin antibody in the preparation of a medicament for the prophylaxis, treatment, prevention or cure of conditions requiring an increase in, or other alteration of, the growth, size, integrity, reproduction and other characteristics of cells, groups of cells, tissues or organs, or for blockade of micrin activity. A disease indication where it might be helpful to neutralise endogenous micrin using an antibody is osteoporosis.

According to a still further aspect of the invention there is provided the use of at least one physiologically active micrin peptide or a micrin-like peptide of the invention, such as a peptide comprising an amino acid sequence according to Formula (I), or preferably comprising an amino acid sequence conforming to that of SEQ ID NO: 1 and/or SEQ ID NO: 2 or a variant thereof for the manufacture of a medicament for the prophylaxis or treatment of conditions requiring reduction of the growth, size, integrity or reproduction of cells, groups of cells, tissues or organs. Micrin treatment may be used in diseases that are characterised by non-malignant tissue overgrowth such as benign prostatic hyperplasia, endometriosis, polycystic ovarian syndrome and polycystic renal disease (see 7b). Micrin may also be useful in reducing tumour burden and in preventing or treating metastases, for example in breast and prostate cancers (see 7a & h). Infertility may also be treatable with micrin, since the endogenous ligand is believed to be involved in the hormonal signalling system at puberty that directs the organism towards reproduction and away from further growth (see 7g & i).

According to another aspect of the invention there is provided the use of an isolated nucleotide sequence coding for a micrin polypeptide of the invention, or a cDNA sequence, a fragment thereof, or an oligonucleotide sequence comprising SEQ ID NO: 16 or functionally equivalent variants thereof, in the preparation of a medicament for the prophylaxis or treatment of conditions requiring reduction of the growth, size or integrity of cells, groups of cells, tissues or organs and in reproductive conditions such as infertility. Micrin gene therapy may also be used for the same disease indications as micrin polypeptides of the invention.

According to a still further aspect of the invention there is provided an isolated peptide comprising the amino acid sequence SEQ ID NO: 1 or SEQ ID NO: 2 or an isolated polynucleotide sequence comprising the sequence defined as SEQ ID NO: 16 for use as a medicament.

Isolated polynucleotide sequences of the invention, expression vectors comprising such nucleotide sequences and antibodies to micrin peptides of the invention can also be used in therapy. Preferably, the nucleic acid, such as RNA or DNA, in particular a native DNA sequence of the invention or a cDNA sequence of the invention, is comprised in an expression vector, which may be expressed in the cells of the individual to be treated. The polynucleotide may comprise naked nucleotide sequences or be in combination with cationic lipids, polymers or targeting systems. The polynucleotide may be delivered by any available technique. For example, the nucleic acid may be introduced by needle injection, preferably intradermally, subcutaneously or intramuscularly. Alternatively, the nucleic acid may be delivered directly across the skin, for example by particle-mediated gene delivery. The nucleic acid may be administered topically to the skin, or to mucosal surfaces for example by intranasal, oral, intravaginal or intrarectal administration. Uptake of nucleic acid constructs may be enhanced by employing transfection techniques commonly used in the art, for example, those including the use of transfection agents. Examples of transfection agents include cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably in the range of 10 µg to 1 mg, per 50 uL of polynucleotide in buffered emulsion, or for particle mediated gene delivery a range of from 1 pg to 10 µg of nucleic acid per delivery unit weight of delivery particles.

Various other applications are also envisaged, for example where suppression of the immune system is required in autoimmune disorders; appetite suppression by stomach shrinkage (using micrin delivered orally) to achieve weight loss; or for the disinhibition of adult stem cells for example in the case of ankylosing spondylitis, rheumatoid arthritis or diabetic retinopathy. Treatment of menorrhagia (excessive menstrual bleeding), uterine fibroids, and ovarian hyperstimulation syndrome with micrin, or the active peptide fragments thereof, are also possible. Micrin may also be used as a contraceptive, for example after suitable N-terminal augmentation (see 71, below). Such applications would be for both veterinary and human prophylaxis and treatment, such veterinary use including use on companion animals.

Micrin or active peptide fragments thereof may be used in further therapeutic applications such as against cancers, for example against tumours, either alone or in combination with other compounds. It may also be used in the treatment of benign overgrowth conditions such as prostatic hyperplasia, and pituitary adenoma. Since micrin and micrin-like polypeptides are capable of suppressing excess proliferation and angiogenesis (see 7f), full length micrin and/or physiologically active peptide fragments thereof may be used to treat certain cystic conditions such as polycystic renal disease. Other conditions that are characterised by excessive angiogenesis, such as psoriasis and endometriosis, may also be treated using peptides of the invention.

Micrin or physiologically active peptide fragments thereof as described herein may also be used in the treatment of other disease, such as cardiac hypertrophy (see 7d), and in the treatment of restenosis and in-stent stenosis. In the treatment of heart failure, micrin therapy may be combined for example with a beta-blocker. The use of a stent to hold a blood vessel open after percutaneous transluminal coronary angioplasty is well known, but its effectiveness is reduced by the formation of in-stent stenosis. Use of a stent from which micrin is eluted offers clinical benefit in suppressing proliferation of muscle cells into the stent (its anti-proliferative effect in vitro on such cells is described herein: see 7e). Micrin may be incorporated into a delayed release carrier, for example in a polymer that slowly dissolves into the body fluids after implantation. Suitable polymers are commonly employed in the art.

Keloids or hypertrophic scars are further targets for potential therapeutic application, and in such cases micrin or active peptide fragments thereof might be applied locally to limit the formation of keloids or to reduce pre-existing lesions. Similarly, micrin or active peptide fragments thereof can be used for the suppression of post-operative scarring in glaucoma.

Micrin or active peptide fragments thereof may be used in the treatment of fungal infections, since micrin may modulate the cell cycle. In the treatment of cancers such as cervical cancer, which are associated with a viral infection, micrin or active peptide fragments thereof may be used as an inhibitor of the host cell cycle.

Micrin antibodies may be used in research and diagnostic tests, prophylaxis and the treatment of disease, and in veterinary applications. The blockade of micrin with an antibody, and hence reduced inhibition of angiogenesis, may be useful in the treatment of certain cardiovascular diseases, and in age-related macular degeneration. Such antibodies may also be used in treatment of renal disease, or of osteoporosis.

Another aspect of the invention is the use of micrin or active peptide fragments thereof, micrin antibodies, or micrin-related genes in homeopathy.

The anti-micrin antibodies according to the invention may be used for example in research and diagnostic measurements and localisations, prophylaxis and treatment of disease, and in veterinary applications. The blockade (i.e. immunoneutralisation) of micrin with an antibody, and hence reduced inhibition of angiogenesis, may be useful in the treatment of various cardiovascular diseases and also in age-related macular degeneration. Antibodies to micrin may also be used to block the progression of renal disease and in the treatment of other disorders (for example, osteoporosis). Thus, anti-micrin antibodies could be used in any disease characterised by micrin excess.

Isolated polynucleotide sequences of the invention relating to the micrins or members of the micrin family as defined and described herein may be used in recombinant micrin production, in gene therapy and/or prophylaxis. Polymorphisms in genes of the micrin family may contribute to a variety of genetic diseases related to abnormalities in organ growth and function. Polymorphisms in genes of the micrin family may also influence treatment decisions for a wide variety of drugs, including micrin-based drugs but also including drugs which may interact with pathways influenced by micrin. Such drugs may be growth factors, but they may also be small molecules or antibodies. Sequences of genes of the micrin family can be used to design and produce diagnostics to detect genetic differences in these genes in patient samples. There are many technologies available for mutation detection which are well known to those in the field. These include differential hybridisation-based assays and mini-sequencing assays. Endpoints include assessments by mass spectrometry, fluorescence and pyrosequencing.

The present invention also relates to use of micrin-depleted or micrin-free sera, as an additive for a culture medium for mammalian cells (including 2-D and 3-D architectures and IVF), tissues, organs ex vivo and whole organisms. Specifically, micrin-depleted sera may be obtained from animals subject to physical disruption of an endocrine or neuroendocrine character, e.g. hypophysectomy. Chemical methods may be used in vivo to inhibit micrin formation and hence the production of micrin-depleted sera from mammals (e.g. cattle, sheep), for example, enzyme inhibition, antisense genomic techniques and administration of hormone antagonists. An alternative approach involves the removal of micrin from sera using, for example, immunoaffinity chromatography or batch binding. Currently serum for such uses is obtained from young animals (such as calves); young and foetal animals produce low levels of micrin. The present invention hence opens the way for the use instead of serum from cheaper and more readily available adult materials, which would otherwise be compromised by the presence of micrin.

The invention will now be described by way of illustration only in the following examples with reference to the accompanying drawings. It is to be understood that the examples and figures are not to be construed as limiting the scope of the invention in any way.

BRIEF DESCRIPTION OF FIGURES

FIG. 7 shows graphically a dose-dependent inhibition by the peptide fragment SEQ ID NO: 2 of MCF7 cell growth as stimulated by IGF1.

FIG. 8: Amino acid and nucleic acid sequence (SEQ ID NO.16) for rat micrin polypeptide FIG. 9: The full nucleotide and polypeptide sequences of SEQ ID NO:32. The sequence corresponding to SEQ ID NO:13 is contained within codons 154-161 of Rat FAM55D GKVTDFNN (SEQ ID NO:34).

DETAILED DESCRIPTION OF INVENTION

1. Protocol for the Purification of Micrin Using Ultrafiltration 1. 1.0 L of sheep plasma (jugular vein, EDTA anticoagulated and azide treated) was coarse filtered through muslin to remove large particulate matter.

2. The filtrate was then passed through a 0.45 μm filter to remove most bacterial and fungal contaminants.

3. The filtrate was then filtered through a 30 kDa Vivaflow 50 tangential flow polyethylene sulphone membrane until roughly 10% of the original volume remained.

4. The filtrate was concentrated over a Millipore 3 kDa membrane regenerated cellulose filter using a stirred cell, to approximately 10-15 ml.

5. The retentate was centrifuged for 30 minutes at 3000 rpm to separate the precipitate.

6. After decanting the supernatant, the pellet was resuspended in 1 ml distilled water and designated 'SPF' (meaning '3-30 kDa sheep plasma filtrate').

It will be appreciated that the method of obtaining pure micrin is not limited to the above purification method for the purposes of the present invention. For example, a method using ion exchange chromatography is also described herein (see 7a, below) and purification may also be accomplished using an antibody to micrin (see 4, below).

2a. Characterisation of Micrin

SPF was subjected to 10-20% tris-tricine sodium dodecyl sulphate polyacrylamide (SDS-PAGE) gel electrophoresis. The gel was stained with Coomassie Blue to visualise the protein present in SPF. The blue bands which appeared on the gel represented the proteins present in SPF. In order to check the molecular mass of the proteins in the bands, appropriate bands were cut out of the gel and placed in elution tubes in a Bio-Rad Model 422 Electro-Eluter, then eluted at 10 mA per band, using a 3500 Da cut-off membrane. The final volume was approximately 250-300 µl.

Figure 1:
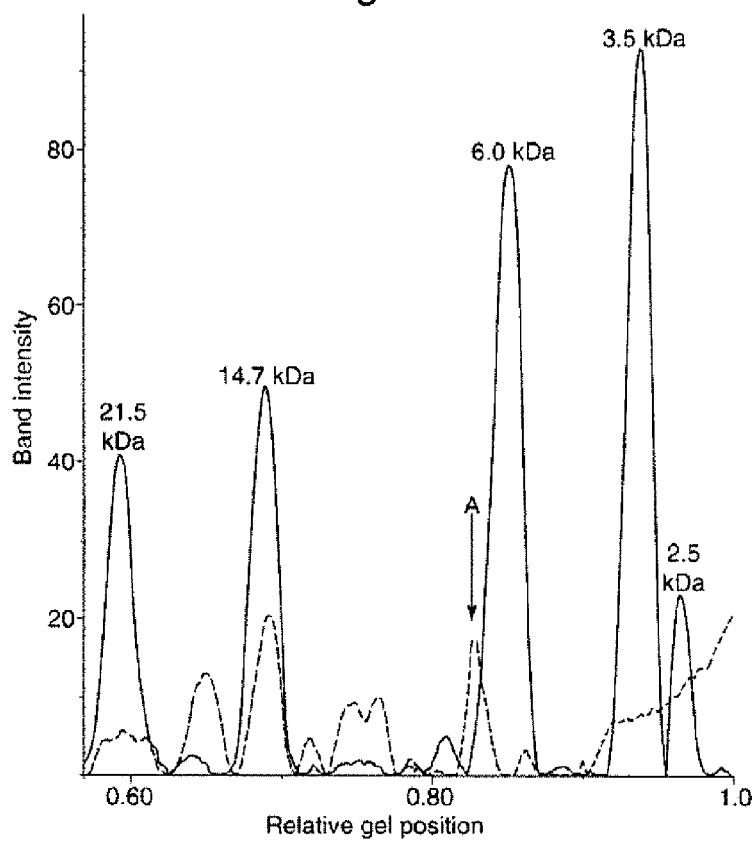
FIG. 1 is a graph showing the gel electrophoretic separation of micrin, as assessed densitometrically, with micrin appearing as a discrete peak at about 7.5 kDa (arrowed 'A')

FIG. 1 shows graphically the result of gel electrophoretic separation of micrin from sheep plasma subjected to the above purification protocol. A gel image was captured digitally, then using a Versadoc 3000 (BioRad, UK) it was analysed using the Quantity-1 software program (BioRad, UK) to determine relative band intensity against known molecular weight markers (denoted peaks). A discrete band on the gel at about 7500 Da produces the peak arrowed 'A' on the graph. An estimation based on the size of this peak as compared with the molecular weight markers of known concentration indicated that micrin probably circulates in blood in nanomolar or lower amounts.

Figure 2:
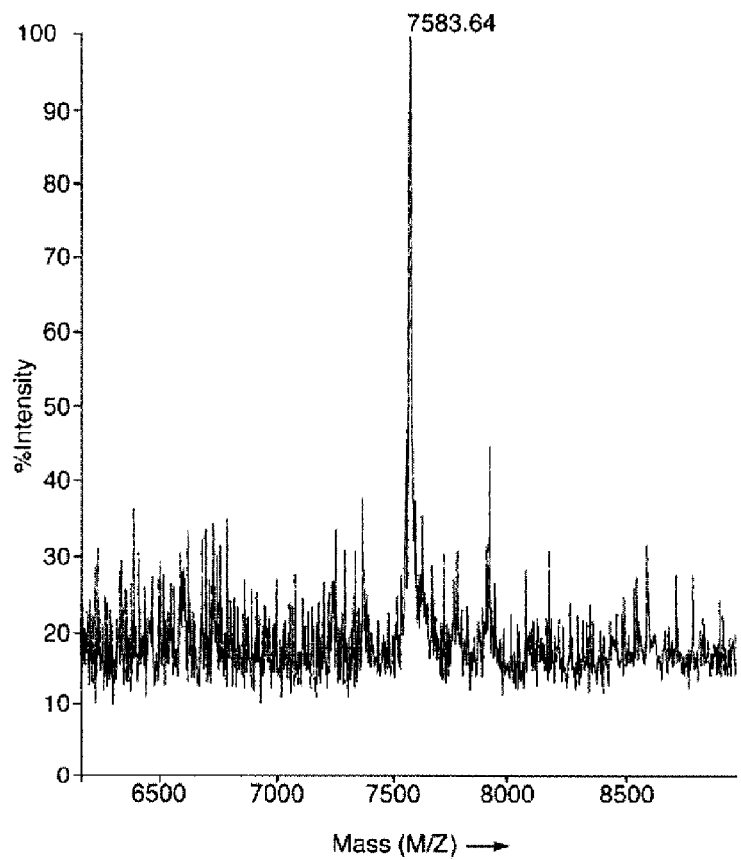
FIG. 2 is a mass spectrum of micrin obtained via ultrafiltration followed by gel electrophoresis.

Referring now to FIG. 2, this shows a mass spectrum for peak 'A' obtained from sheep plasma subjected to purification by the above purification protocol followed by gel electrophoresis. The mass spectrum was obtained on a PerSeptive Biosystems Voyager DE Pro MALDI-TOF mass spectrometer, using sinapinic acid as matrix and calibrated against carbonic anhydrase. There was a single well-defined peak at 7583.6. The protein at this peak had the biological activities of micrin.

2b. Effect of Trypsin on Micrin

The inventor has determined that trypsinisation partially reduces micrin activity in vitro (data not shown), using an assay of bone marrow stem cell viability (for method reference see 7e, below). This indicates that the molecule is proteinaceous in character. It also indicates that the whole molecule is not required for activity, a conclusion supported by the observation of biological activity associated with the micrin peptide fragment, SEQ ID NO: 9 (see 7c, 7g and 71, below) and a part thereof (see 7i, below).

2c. Identification of Fragments of the Micrin Peptide

For Edman degradation similar gels were transferred to PVDF membranes and stained with Coomassie Blue. The appropriate band at about 7500 Da was then excised and subjected to automated Edman degradation reaction (Applied Biosystems Process). Peak A was subjected to Edman degradation (which yields N-terminal sequence data) in order to ascertain the amino acid sequence. This sequence was found to contain SEQ ID NO. 1.

Preferably, SEQ ID NO. 1 takes the form of

| S K P L T G K V K E F N N I; | SEQ ID NO. 7 |
| D K P L T G K V K E F N N I; | SEQ ID NO. 8 |
| or | |
| M K P L T G K V K E F N N I | SEQ ID NO. 9 | and the sequence (SEQ ID NO: 2):

```
      5    10   15   20
1 KPLTGKVKEFNNIKGFXVI
``` wherein 1 is either S, D, or M; and
'X' represents an amino acid residue of unknown identity.

2d. Determination of the Isoelectric Point of Micrin

The isoelectric point of micrin was determined using a two-dimensional gel separation and blotting technique. SPF was separated in the first dimension using 3-110 pI IEF strips (BioRad, UK) and then separated in the second dimension using 12.5% tris-HCl SDS-PAGE gels. The resulting gel was then transferred to PVDF membrane and probed with the micrin peptide with the micrin peptide fragment SEQ ID NO: 1 antibody and visualised with chemiluminescence (Pierce Supersignal West Femto).

The isoelectric point of micrin was determined as pH 6.5.

3. Determination of the Nucleotide Sequence for Micrin

A variety of RTPCR and RACE-based techniques were attempted in order to obtain DNA sequence data For instance, the degenerate 5' primer:

```
    GTNAARGARTTYAAYAAYAT        SEQ ID NO. 10
``` corresponding to amino acid sequence VKEFNNI (SEQ ID NO. 11), was modified by the addition of a sacII restriction site to the 5' end of this sequence in order to raise the annealing temperature of the resulting primer for efficient amplification during polymerase chain reaction (PCR) to produce the primer:

```
    CCGCGGTNAARGARTTYAAYAAYAT       SEQ ID NO: 12
``` wherein
R is A or G;
Y is C or T; and
N is A, G, C, or T.

An alternative variant of SEQ ID NO: 10:

```
    GGNAARGTNACNGAYTTYAAYAAY        SEQ ID NO: 13
``` corresponding to the amino acid sequence KVTDFNN (SEQ ID NO. 14) in combination with a 3' RACE primer such as:

```
    GCGGCCGCTTTTTTTTTTTTTTTTTTT     SEQ ID NO: 15
``` is able to amplify in a PCR reaction a DNA fragment from rat hypothalamic total cDNA corresponding to the micrin amino acid sequence.

Two rat hypothalamuses are used to extract total RNA which is used for cDNA synthesis using an oligo-dT primer under standard conditions. The cDNA is diluted one in ten and used as a template for PCR.

Touch down PCR is used to amplify candidate micrin sequences. The conditions are, 15 cycles of denaturation (94° C., 60 sec), annealing (65° C., 30 sec), and elongation (72° C., 60 sec), and after each cycle the annealing temperature is reduced by 1° C. This was followed by a further 20 cycles whose conditions were: denaturation (94° C., 60 sec), annealing (50° C., 30 sec), and elongation (72° C., 60 sec). A single amplification product is obtained with an apparent electrophoretic mobility on a 1.5% agarose-TBE gel of 200 nucleotides. This is re-amplified using 30 cycles of denaturation (94° C., 60 sec), annealing (50° C., 30 sec) and elongation (72° C., 60 sec). The resulting PCR is cloned into a Topo-cloning vector for sequencing. Sequencing is accomplished in both the forward and reverse orientations using M13 primers flanking the cloning site in the Topo-vector.

The resulting sequence obtained, beyond the primer sequence, is shown in FIG. 8, as is the corresponding amino acid sequence. The full nucleotide and polypeptide sequences (SEQ ID NO:32) are shown in FIG. 9 with the primer relating to codons 154-161.

The polynucleotides of the invention can hybridize to the coding sequence or the complement of the coding sequence as shown in FIG. 9 at a level significantly above background. Background hybridization may occur, for example, because of other DNAs present in a DNA library. The signal level generated by the interaction between a polynucleotide of the invention and the coding sequence or complement of the coding sequence as shown in FIG. 9 is typically at least 10 fold, preferably at least 100 fold, as intense as interactions between other polynucleotides and the coding sequence as shown in FIG. 9. The intensity of interaction may be measured, for example, by radiolabelling the probe, e.g. with $^{32}P$. Selective hybridisation may typically be achieved using conditions of medium to high stringency. However, such hybridisation may be carried out under any suitable conditions known in the art (see Sambrook et al, "Molecular Cloning: A Laboratory Manual", 1989). For example, if high stringency is required, suitable conditions include from 0.1 to 0.2×SSC at 60° C. up to 65° C. If lower stringency is required suitable conditions include 2×SSC at 60° C.

The coding sequence as shown in FIG. 9 may be modified by nucleotide substitutions, and/or by one or more insertions and/or deletions and/or by an extension at either or both ends. Additional sequences such as signal sequences may also be included. The modified polynucleotide generally encodes a polypeptide which has micrin activity. Degenerate substitutions may be made and/or substitutions may be made which would result in a conservative amino acid substitution when the modified sequence is translated.

A nucleotide sequence which is capable of selectively hybridising to the complement of the DNA coding sequence as shown in FIG. 9 will generally have at least 60%, at least 70%, at least 80%, at least 90%, at least 95%, at least 98% or at least 99% sequence identity to the coding sequence as shown in FIG. 9 over a region of several contiguous nucleotides or most preferably over the full length of the sequence shown in FIG. 9.

For example the UWGCG Package provides the BESTFIT program, which can be used to calculate homology (for example used on its default settings) (Devereux, J. et al, *Nucleic Acids Research* 12, 387-395, 1984). The PILEUP and BLAST algorithms can be used to calculate homology or line up sequences (typically on their default settings), for example as described in Altschul, S. F., *J. Mol. Evol.*, 36:290-300, 1993; Altschul, S. F. et al, *J. Mol. Biol.*, 215:403-10, 1990.

Any combination of a specified degree of sequence identity and minimum size may be used to define polynucleotides of the invention, with the more stringent combinations (i.e. higher sequence identity over longer lengths) being preferred. Thus, for example a polynucleotide which has at least 90% sequence identity over 25, preferably over 30 nucleotides forms one aspect of the invention, as does a polynucleotide which has at least 95% sequence identity over 40 nucleotides.

Polynucleotide fragments, such as those suitable for use as probes or primers will preferably be at least 10, preferably at least 15 or at least 20, for example at least 25, at least 30 or at least 40 nucleotides in length.

Polynucleotides according to the invention may be produced recombinantly, synthetically, or by any means available to those of skill in the art. They may also be cloned by standard techniques. The polynucleotides are typically provided in isolated and/or purified form.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15-30 nucleotides) to a region of the micrin gene which it is desired to clone, bringing the primers into contact with DNA obtained from a suitable cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Such techniques may be used to obtain all or part of the micrin gene sequence described herein. Although in general the techniques mentioned herein are well known in the art, reference may be made in particular to Sambrook et al, as cited above.

4. Raising Antibodies to Micrin

Two peptides were synthesised based on SEQ ID NO: 1 (Peptides 1 and 2) and two based on SEQ ID NO: 2 (Peptides 3 and 4), as follows.

Peptide 1: The 14 amino acid sequence, designated Peptide 1, for use in competition studies:

```
     MKPLTGKVKEFNNI            SEQ ID NO. 9
```

Peptide 2: A Cys-conjugated peptide at the N-terminus to allow conjugation to hapten (Keyhole Limpet Haemocyanin, KLH, or thyroglobulin) for antibody production, designated Peptide 2:

```
     CMKPLTGKVKEFNNI           SEQ ID NO. 18
```

The 20 amino acid sequence, designated Peptide 3, for use in competition studies is:

```
     MKPLTGKVKEFNNIKGFGVI      SEQ ID NO. 19
```

A Cys-conjugated peptide at the N-terminus to allow conjugation to hapten (Keyhole Limpet Haemocyanin, KLH) for antibody production, designated Peptide 4 is:

```
     CMKPLTGKVKEFNNIKGFGVI     SEQ ID NO. 20
```

The peptides were synthesised using Fmoc solid phase synthesis using a Milligen peptide synthesiser (Model 9050).

Polyclonal antibodies were raised using Peptide 2 and Peptide 4 by injection into rabbits as follows: Peptides 2 or 4 conjugated to hapten in neutral buffer (PBS) were mixed with an equal volume of complete or incomplete Freund's adjuvant, as indicated below. An emulsion was formed by passage through a 23G needle to reach a consistency that did not separate on standing. The emulsion was injected into rabbits according to the following schedule.

The 1st subcutaneous injection consisted of 400 μg of Peptide 2 per rabbit in 100 μl PBS mixed with 100 μl of Freund's complete adjuvant. Subsequent injections were identical, except for the use of incomplete adjuvant instead of complete adjuvant. In one case two further injections were performed at approximately 3 and 7 weeks after the first injection were performed. In another case four further injections were performed at approximately 3, 7, 11 and 15 weeks after the first injection. Test bleeds were taken at approximately 8 and 12 weeks after the first injection and a terminal bleed-out occurred 17 weeks after the first injection.

All antisera were subjected to evaluation against Peptide 2 or Peptide 4 by competition ELISA, using standard methodology. In immunohistochemistry, pre-absoprtion studies have been undertaken successfully, for example using an incubating concentration of SEQ ID NO: 1 at 100 μg/ml (Haylor J. L. et al, 2009, *Regulatory Peptides*, 152, 48-53).

Polyclonal antibodies were raised in the same manner using goats instead of rabbits, with Peptide 2 conjugated to KLH. The primary immunisation was followed by 8 boosters at monthly intervals, using standard techniques for the raising of polyclonal antibodies. Titre was established via immuno-histochemistry, using rat and ovine median eminence tissue and the ability to block antibody with Peptide 1 was determined on histological sections. Specificity was tested using a range of hypothalamic peptides. Epitope mapping using dot blots showed that the goat antibody, purified with protein G, recognised an epitope in the C-terminal 8 amino acids of SEQ ID NO. 9, which consists of KVKEFNNI (SEQ ID NO. 21). Purification of the antibody using the peptide SEQ ID NO: 9 immobilised on a column enriches for antibody to the C-terminal epitope. The goat antibody has been used in connection with an assay based on adult rat bone marrow stem cells in culture, with α-MEMS as cell medium and manual assessments of cell numbers and morphology using time-lapse video photography over 24 h. In this assay, an aqueous extract of rat hypothalamus has a negative effect on cell proliferation. Immunodepletion and, separately, in-assay immunoneutralisation with the goat antibody both reduce this negative influence, a reduction that itself can be reversed by co-administration with the peptide SEQ ID NO: 9. Sheep serum also has a negative effect on cell proliferation in this in vitro assay, notably a sub-10 kDa fraction, and immunodepletion with the goat antibody reduces this effect as well.

Monoclonal antibodies were raised in mice by a similar technique (Kohler, G. and Milstein, C., *Eur. J. Immunol*, 6, 511-519, 1976; Milstein, C., *Immunol Today*, 21, 359-364, 2000). Mice were immunised with Peptide 2. Sera from the mice were tested for binding with Peptide 1. Spleen cells from positive animals were fused with myeloma cells and the fusates sequentially cloned to prepare a monoclonal antibody, which was then grown in bulk.

Figure 3:
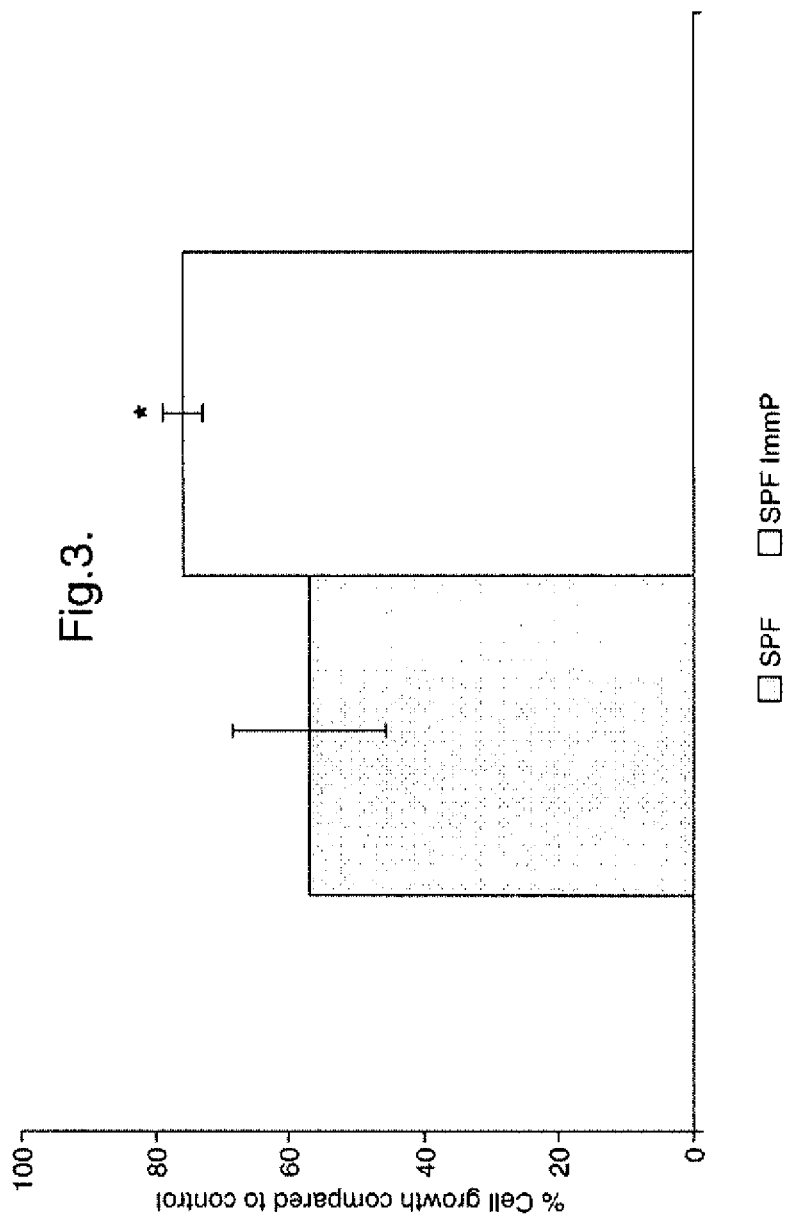
FIG. 3 is a graph showing the effects of a 3-30 kDa sheep plasma fraction ('SPF') on MDA-MB231 breast cancer cell growth following removal of micrin using immunoaffinity separation.

Partial removal of micrin was achieved using the rabbit antiserum to the micrin peptide fragment (SEQ ID NO: 9), an immunoprecipitation approach, as is now described. SPF was immunoprecipitated with antibody and protein A with the 2nd bleed of antiserum diluted 1 in 10. Cellular growth of MDA-MB231 breast cancer cells in response to SPF and immuno-precipitated SPF (SPF ImmP) was assessed using a standard Alamar Blue assay, of the kind described below for prostate and breast tumour cells. The inhibitory effect of SPF on cell viability was significantly inhibited by prior immunoprecipitation (FIG. 3; the asterisk denotes a significant difference, $p<0.05$, paired t-test). Neither PBS nor normal rabbit serum (10%), substituted for SPF, affected cellular growth of these MDA-MB231 cells (data not shown).

This is evidence that serum that is depleted in micrin or micrin-free, in this case by use of an antibody, would be beneficial for use as an ingredient of a cell culture medium.

Figure 4:
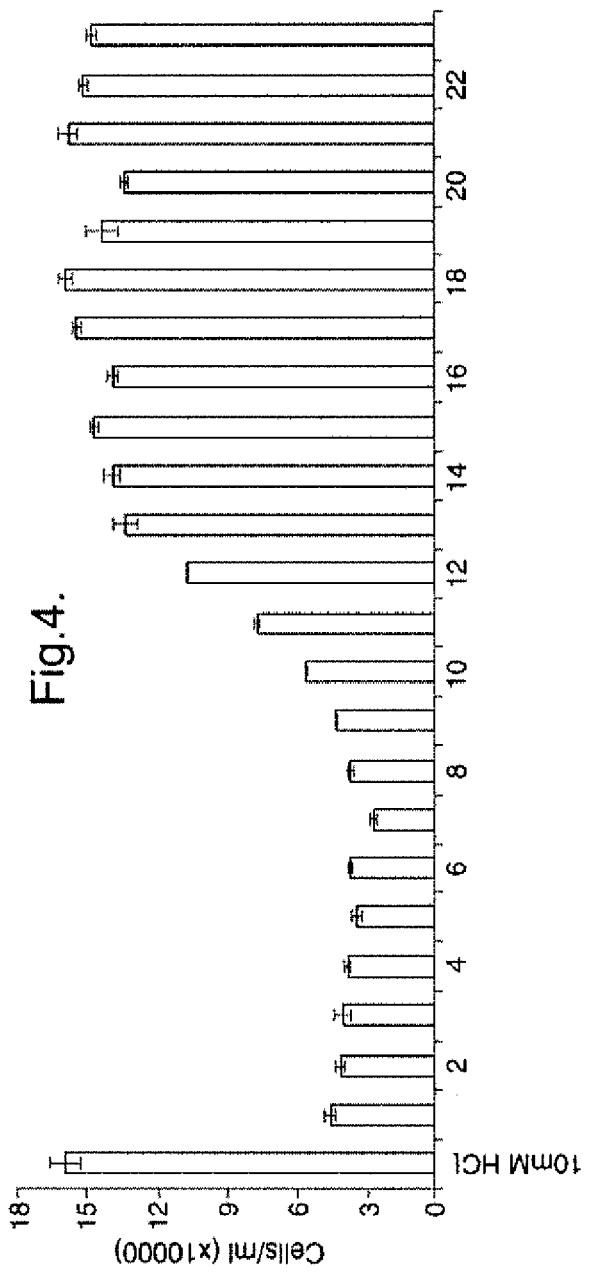
FIG. 4 is a graph showing the effects on cell growth of fractions of SPF run down an affinity chromatography column to which is bound an antibody to the micrin peptide fragment SEQ ID NO: 9.

For the purification of micrin, a rabbit antibody to the micrin peptide fragment was linked covalently to CNBr-Sepharose 4 MB solid phase support using standard techniques. 30 ml of SPF was applied to a column of this material, and bound antigen was then eluted in 10 mM HCl. Fifty fractions of 0.5 ml each were collected and assayed for their effects on MDA-MB231 breast cancer cell growth, at 10% dilution. Cells were grown in the presence of these fractions for 72 hours then counted by Coulter Counter. Referring to FIG. 4, those fractions containing micrin caused cell growth inhibition, as shown.

The antibodies to the micrin peptide fragment have also been used in immunohistochemistry using standard techniques. Immuno-staining was clearly apparent in the hypo-thalamus, consistent with local production and secretion; staining was especially seen within the arcuate nucleus with axonal varicosities of micrin also clearly visible in the median eminence. Immuno-staining was also apparent in neuroendocrine cells throughout the body, as indicated by co-localisation studies involving chromogranin A.

The antibodies described above may be used in purification, isolation or screening methods or indeed as therapeutic agents in their own right, as well as in the production of micrin-free cell culture media. Antibodies may be raised against the specific epitopes of the polypeptides. An antibody, or other compound, 'specifically binds' to a protein when it binds with preferential or high affinity to the protein for which it is specific but substantially does not bind, or binds with only low affinity, to other proteins. A variety of protocols for competitive binding or immunoradiometric assays to determine the specific binding capability of an antibody are well known in the art (see for example Maddox et al, *J. Exp. Med.*, 158, 1211-1226, 1993). Such immunoassays typically involve the formation of complexes between the specific protein and its antibody and the measurement of complex formation.

Antibodies of the invention can be produced by any suitable method. Means for preparing and characterising monoclonal and polyclonal antibodies are well known in the art, see for example Harlow and Lane "Antibodies: A Laboratory Manual", Cold Spring Harbor Laboratory Press, Cold Spring Harbor, N.Y., 1988. For example, an antibody may be produced by raising antibody in a host animal against the whole polypeptide or a fragment thereof, for example an antigenic epitope thereof.

Antibodies, both monoclonal and polyclonal, which are directed against polypeptides of the invention are particularly useful in diagnosis.

Antibodies may be used in a method for detecting polypeptides of the invention in a biological sample. Generally such a method comprises (a) incubating a biological sample with the antibody under conditions which allow for the formation of an antibody-antigen complex; and (b) determining whether antibody-antigen complex comprising the antibody is formed. A sample may be for example a tissue extract, blood, serum or saliva. Antibodies or polypeptides of the invention may be bound to a solid support and/or packaged into kits in a suitable container along with suitable reagents, controls, instructions, etc. Antibodies or polypeptides may be linked to a revealing label and thus may be suitable for use in methods of in vivo imaging.

An antibody to micrin or a fragment thereof may be used to achieve purification in sufficient quantities for biological testing, as described above, but also for chemical characterisation, as will now be described.

An ImmunoPure protein G IgG Plus Orientation' kit (Pierce, Rockford II) is used to make an antibody affinity column. Briefly: 2 ml of immobilised protein G 50% slurry is bound to saturation (approximately 10 mg) with antibody from goat antiserum raised against Peptide 2. Bound antibody is covalently linked to the matrix according to the manufacturer's instructions. The hypothalami and pituitary glands are dissected out of a mixed population of 250 rats and rapidly frozen in liquid nitrogen. These tissues are then ground to a paste using an homogeniser, re-suspended in phosphate-buffered saline solution (PBS) containing a protease inhibitor cocktail and subjected to 3×20 s pulses of sonication. Insoluble material is removed by sedimentation at 23 200×g for 2 h. The supernatant is applied to the affinity column by gravity feed after which the column is washed in PBS and bound protein eluted in 1 ml batches with 0.1M glycine pH 2.8. Fractions are analysed by 15% SDSPAGE and Western Blot using the same protein G-purified goat antibody. Bands are either excised for mass spectrometry or are blotted onto membrane for N-terminal Edmund degradation. for sequence confirmation. Western blot analysis reveals two key bands of around 40 kDa and 5-7 kDa, the latter being a processed form of the former, which are both sensitive to antibody pre-absorption by Peptide 1 (SEQ ID NO. 9) and separately to the C-terminal half thereof, KVKEFNNI (SEQ ID NO. 21).

The amino acid sequence of the rat polypeptide and corresponding nucleic acid sequence is determined as shown in FIG. 8.

5. Production and Modification of the Whole Micrin Peptide

The whole micrin peptide may be prepared using standard techniques by heterologous expression from suitable recombinant DNA constructs in a suitable host cell. These expression systems are used routinely to manufacture biopharmaceuticals and the processes used to manufacture them have been thoroughly validated.

The proteins and peptides of the invention may also be made synthetically or by recombinant means as discussed below.

The amino acid sequence of proteins and polypeptides of the invention may be modified to include non-naturally occurring amino acids or to increase the stability of the compound. When the proteins or peptides are produced by synthetic means, such amino acids may be introduced during production. The proteins or peptides may also be modified following either synthetic or recombinant production.

The proteins or peptides of the invention may also be produced using D-amino acids. In such cases the amino acids will be linked in reverse sequence in the C to N orientation. This is conventional in the art for producing such proteins or peptides.

A number of side chain modifications are known in the art and may be made to the side chains of the proteins or peptides of the present invention. Such modifications include, for example, modifications of amino acids by reductive alkylation by reaction with an aldehyde followed by reduction with $NaBH_4$, amidination with methylacetimidate or acylation with acetic anhydride.

6. Assays to Detect Micrin

6a. In Vitro Assay

Micrin activity has been determined by means of a suitable in vitro assay, for example the breast cancer cell viability assay described above in Section 4 with reference to FIG. 4. A useful assay in support of molecular optimisation involves adult rat bone marrow stem cells in culture, with α-MEMS as cell medium and manual assessments of cell numbers and morphology using time-lapse video photography over 24 h. In one study, untreated control cells increased in number by 50%. An increase of just under 20% was also seen with the 14 mer peptide SEQ ID NO: 9, administered at 10 μg/ml of medium. In contrast, a reduction by about 80% in cell numbers was seen with the 20 mer peptide SEQ ID NO: 19, due to apopotosis.

6b. Enzyme Linked Immunosorbent Assay (ELISA)

Direct measurements of micrin levels have been made using an ELISA, now described, this being a typical example of an immunoassay which can be used for micrin measurements. The peptide fragment of micrin (SEQ ID NO: 9) was adsorbed (for 16 hours at 4° C.) onto the wells of a 96-well plate. Standards (i.e. dilutions of micrin peptide fragment) or samples (plasma or other body fluids or tissue extracts) were mixed with a fixed concentration of antibody for 16 hours at 4° C. This mixture was then added to the blocked, washed and drained coated wells in triplicate and incubated for 2 hours at room temperature. In this technique, any unbound antibody in the mixture can bind to the immobilised micrin peptide fragment on the plate. The amount of free antibody is dependent on the amount of micrin in the mixture. Thus, the more micrin in the sample or standard, the less free antibody available. The plates were then washed and drained, following which an appropriate concentration of secondary (anti-rabbit) antibody was added and incubated for 1 hour at room temperature. After washing and draining the plates, TMB One (Promega) was added to each well (10 mins) followed by sulphuric acid. The colour reaction was read immediately in an ELISA Plate reader at 620 nm. The above procedure is in accordance with standard ELISA practice (Nagai, R., *J. Biol. Chem.*, 277(50): 48905-48912, 2002), and used Reactibind microtitre plates as recommended for this type of competitive assay (from Pierce Biotechnology, Rockford, Ill.).

An ELISA assay of 5 male and 5 female plasma samples indicated that plasma micrin levels for males were in the range 8.6-59.0 nmol and for females 3.5-18.4 nmol, the difference being statistically significant (p<0.05 Student's t-test).

6c. Other Assays

A protein or peptide of the invention may be labelled with a revealing label to allow it to be detected. Suitable labels include radioisotopes such as $^{125}I$, $^{35}S$ or enzymes, antibodies, polynucleotides and linkers such as biotin. Labelled polypeptides of the invention were used in diagnostic procedures such as immunoassays. In such assays it may be preferred to provide the peptides attached to a solid support, for example, the surface of an immunoassay well or dipstick. Such labelled and/or immobilized polypeptides may be packaged in the form of a kit in a container. The kit may optionally contain other suitable reagents, controls or instructions and the like.

7. Examples

7a. Micrin Reduces Tumour Cell Viability

The effects of micrin on viability of tumour cells were determined using MCF7 breast cancer cells and PC3 prostate cancer cells. Cells were plated out to provide $2\times10^4$ cells in 2 $cm^2$ wells in Dulbecco's modified Eagles medium (DMEM) containing 10% foetal calf serum (FCS), antibiotics and a stabilised substitute for glutamine (Glutamax, Invitrogen UK). The cells were allowed to attach overnight. The medium was removed and the cells were washed several times with fresh medium, and then treated with test or control samples diluted in medium.

Test and control samples were produced according to an ion exchange method using 120 ml sheep ovarian follicular fluid as the starting material. Follicular fluid obtained by aspiration of abattoir-derived sheep ovaries was centrifuged at +4° C. and 2000 g for 10 minutes, then spun through Amicon Centriprep-30 cartridges at 1800 g to give a nominal 0-30 kD fraction. This fraction was spun through Amicon Centriprep-3 cartridges to give a nominal 3-30 kD sub-fraction. This fraction was concentrated and gel filtered through a Pharmacia Superdex-75 column to give a nominal 10-20 kD sub-fraction. This sub-fraction was diluted with buffer and concentrated and applied to a Vydac's Protein SAX HPLC ion exchange column and eluted with a gradient of 0-1M NaCl. Elutant fractions (35×1 ml) were collected and validated for the exclusive presence of micrin as judged by mass spectrometric identification of the c7500 Da peptide (fractions 28 and 29). Micrin-free control samples having no detectable micrin were selected from slightly earlier running fractions (fractions 24 and 25) with equivalent salt concentration.

Camptothecin, an inducer of apoptosis, was used as a positive control at 3 μmol. After 48 hours the medium was changed for fresh medium and the number of remaining viable cells was quantitated using Alamar Blue. The number of viable cells in the micrin and camptothecin samples were expressed as a percentage of the number of viable cells in the micrin-free control samples. The tests were conducted in triplicate. The data in Table 1 below show that Camptothecin reduced the viability of the PC3 and MCF7 cells to 43.9 and 56.2% respectively. A greater effect was seen with micrin, with only 14.3 and 41.7% viability for the two cell lines respectively.

TABLE 1

| Treatment | Viability (% micrin-free control) Mean (n = 3) SEMs < 5% | |
|---|---|---|
| | PC3 (prostate cancer) | MCF-7 (breast cancer) |
| Micrin | 14.3 | 41.7 |
| Camptothecin | 43.9 | 56.2 |

Induction of apoptosis by micrin was subsequently confirmed by Annexin V staining and flow cytometry (data not shown).

7b. Micrin Reduces Compensatory Renal Growth

The action of micrin was demonstrated by an in vivo bioassay in the rat, involving inhibition of compensatory renal growth after unilateral nephrectomy (Thomas, G. L. et al., *Nephrol. Dial. Transpl.*, 13: 2216-2226, 1996).

Male Wistar rats (250-350 g) were subjected to left nephrectomy through a left flank incision, after being anaesthetised with halothane, and the excised kidney was weighed. Three batches of test material containing micrin and micrin free control samples were produced by the method given in 7a. The test and control materials were infused continuously (5 μl/hr) into the pelvic region of the remaining kidney via a perforated catheter using an osmotic mini-pump (Alzet 2 m12, Alza Corporation, US). After 7 days the remaining kidney was removed and weighed.

The wet and dry weight and total kidney protein and DNA content in the right and left kidneys was measured. Each parameter was expressed as value for the right kidney (post treatment) as a percentage of that in the left kidney (pretreatment). Data were compared using Student's t-test (equal variance).

Table 2 shows partial inhibition of compensatory growth by exogenous micrin in the unilaterally nephrectomised male rats, compared with controls.

TABLE 2

| Compensatory renal growth | Control right/left kidney (%) Mean ± SEM | Micrin right/left kidney (%) Mean ± SEM | Students t-test (equal variance) |
|---|---|---|---|
| Kidney wet weight (% change) | 41.7 ± 2.7 | 23.2 ± 2.6 | p < 0.005 |
| Kidney dry weight (% change) | 25.9 ± 5.9 | 13.5 ± 1.1 | p < 0.012 |
| Protein (% change) | 65 ± 49 | 28 ± 14 | p < 0.2 |
| DNA (% change) | 81 ± 23 | 42 ± 15 | p < 0.05 |

Using surgical and experimental procedures as in 7c below, it has been shown that, like the whole micrin molecule, the micrin peptide fragment, SEQ ID NO: 9, inhibits compensatory renal growth (Haylor J. L. et al, 2009, *Regulatory Peptides*, 152, 48-53).

7c. An Anti-Micrin Antibody Increases Compensatory Renal Growth

Administration of a monoclonal antibody raised to the micrin peptide fragment (SEQ ID NO: 9) has been demonstrated in an in vivo bioassay in the rat. Treatment increased the compensatory renal growth after subtotal nephrectomy (removal of approximately 69% of the total kidney mass). (Haylor J. L. et al, 2009, *Regulatory Peptides*, 152, 48-53)

The top and bottom poles of the left kidney of male Wistar rats (250-350 g) were removed through a left flank incision, under halothane anaesthesia. A perforated cannula was inserted into the renal cortex from pole to pole and attached to an osmotic mini-pump (Alzet 2 m12, Alza Corporation, US) implanted into a subcutaneous pocket. The rats were infused via the pump (5 μl/hr) continuously for 14 days with either (a) anti-micrin mouse monoclonal antibody or (b) isotonic saline (0.9%). The mouse monoclonal antibody was diluted to 40% in isotonic saline prior to use. Three days later, the right kidney was removed through a right flank incision, under anaesthesia, generating a model of subtotal nephrectomy. The right kidney was weighed and twice this weight was assumed to be the original kidney mass prior to treatment. After a further 11 days the animal was killed by exsanguination and the remnant left kidney was removed and weighed. The protein and DNA content of the kidney was determined from a 20% tissue homogenate.

For each animal the extent of nephrectomy was expressed as the weight of kidney tissue removed (weight of left kidney tissue removed plus weight of right kidney at removal) as a percentage of the original kidney mass. This was similar for the two treatment for groups (68.4±1.2% for control; 69.0±1.2% antibody treated, Mean±SEM (n=4)) indicating that both had a similar stimulus for growth.

For each parameter, data for each animal obtained from the left remnant kidney was expressed as a percentage of the value for the right kidney at nephrectomy. Composite growth was expressed as the average of wet weight % change, protein % change and DNA % change. Data were compared using Student's t-test (equal variance).

The data in Table 3 show that treatment with the anti-micrin monoclonal antibody enhances compensatory renal growth.

The antibody is immunoneutralising endogenous micrin, which plays an inhibitory role in compensatory renal growth.

TABLE 3

| Compensatory Renal Growth | Control left remnant/ right kidney (%) Mean ± SEM (n = 4) | Anti-micrin antibody left remnant/ right kidney (%) Mean ± SEM (n = 4) | Student's t-test (equal variance) |
|---|---|---|---|
| Kidney wet weight (% change) | 66.6 ± 12.4 | 94.0 ± 9.75 | p < 0.066 |
| Protein (% change) | 47.5 ± 9.5 | 68.3 ± 3.7 | p < 0.044 |
| DNA (% change) | 65.0 ± 17.3 | 108.3 ± 15.1 | p < 0.054 |
| Composite Growth (% change) | 59.7 ± 11.3 | 90.2 ± 4.1 | p < 0.022 |

7d. Micrin Reduces Cardiac Hypertrophy

Micrin was shown to inhibit cardiac hypertrophy in vitro. Atrial natriuretic factor (ANF, a marker of hypertrophy) was measured in relation to GAPDH (glyceraldehydes 3-phosphate dehydrogenase, a housekeeping gene and an indicator of equal RNA loading).

Cardiac myocytes were prepared from Wistar rat pups aged 2-3 days according to established methods (Vara, D. et al, *J. Biol. Chem.*, 278(24):21388-21394, 2003). Non-myocytes and myocytes were separated by preplating for 30 minutes onto 10 cm$^2$ Primaria tissue culture plates (Falcon, UK), in media containing 68% DMEM-Glutamax, 17% M199 (Gibco BRL, US), 15% FCS and 100 µg/ml penicillin/streptomycin, with myocytes remaining in the supernatant. This method is used routinely to prepare viable neonatal cardiac myocytes and typically results in preparations containing 97-99% cardiac myocytes as determined by light microscopy and immunostaining with a cardiospecific troponin I antibody.

Cardiac myocytes then were plated at a cell density of 3×10$^6$ in 10 cm$^2$ Primaria culture dishes (BD Biosciences, UK) and maintained in a medium containing DMEM/5% FCS/100 µg/ml penicillin/streptomycin/500 µmol bromodeoxyuridine for 24 hours. Myocytes were serum-starved for 48 hours in a medium containing DMEM, 100 µg/ml penicillin/streptomycin and 0% FCS. Test and control materials were obtained using 120 ml sheep follicular fluid according to the method given in Example 7a. The test material and control material were diluted 1:11 in growth medium before being added to the cells. Cells then were treated with medium containing 0% FCS (base conditions) or 20% FCS (to induce cardiac hypertrophy) in the presence or absence of test or control materials for 24 hours.

Total RNA was prepared from myocytes using the RNeasy Mini-Kit as recommended by the manufacturer (Qiagen, UK). Total RNA samples initially were treated with DNase 1 to remove any contaminating genomic DNA according to standard procedures. From each sample 5 µg of DNase-free total RNA was then reverse-transcribed using a cDNA Cycle Kit (Invitrogen, UK). Following ethanol precipitation, cDNA samples were dissolved in 20 µl double-distilled RNase-free water. 1 µl of this diluted cDNA was used for polymerase chain reaction (PCR) amplification of cDNA molecules specific for ANF and GAPDH. PCR was performed using 1 µl of diluted cDNA in a total volume of 20 µl containing 50 mM HEPES (pH 7.9), 1.5 nmol MgCl$_2$, 100 µmol of each dNTPs, 1 U Taq polymerase and 1 mmol each of sense and antisense primers. Primers were directed against the human sequence for ANF (forward 5'-ATGGGCTCCTTCTCCATCAC-3' (SEQ ID NO. 22); reverse 5'-TCTTCGGTACCGG-GAAGCT-3' (SEQ ID NO. 23)). Primers for GAPDH (forward 5'-CCTTCATTGACCTCAAC-3' (SEQ ID NO. 24); reverse 5'-AGTTGTCATGGATGACC-3' (SEQ ID NO. 25)) were used for each sample as an internal control for mRNA integrity and equal loading. PCRs were carried out for GAPDH according to previously published methods (Vara, D. et al, *J. Biol. Chem.*, 278(24):21388-21394, 2003) using 28 cycles of amplification which results in the exponential phase of amplification for this gene. PCRs were carried out for ANF as follows: 1 cycle at 94° C. for 2 minutes; then 22 cycles of 94° C. for 30 seconds/63° C. for 30 seconds/72° C. for 60 seconds. The reaction was completed with a final extension cycle of 72° C. for 10 minutes. PCR products were separated in 1% v/v agarose gels. These were stained in 40 µg/ml ethidium bromide for 5 minutes and stained bands were viewed and photographed under ultraviolet light.

Photographs were scanned digitally and the intensity of resultant bands determined densitometrically using the Quantity-1 software program (BioRad, UK).

Figure 5:
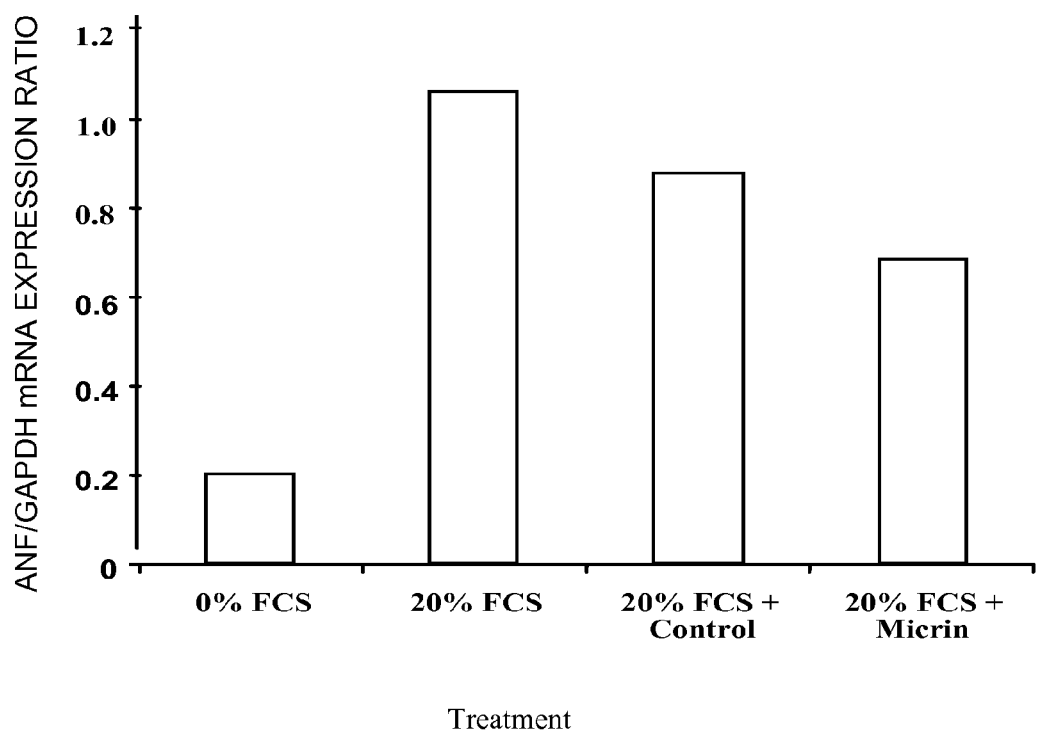
FIG. 5 is a graph showing the inhibition by micrin of the hypertrophy of cardiac myocytes in vitro.

Results were calculated by determination of the ANF: GAPDH expression ratios. These are shown in FIG. 5, to which reference is now made. In the base case (0% FCS), this ratio is low (about 0.2). In the three cases in which FCS was provided the ratio is significantly higher, showing that hypertrophy occurred. With micrin treatment the ratio was approximately 0.7, as compared with about 1.0 or more for controls (FCS alone or FCS plus micrin free control). It is thus demonstrated that micrin inhibits the development of hypertrophy in cardiac myocytes.

7e. Micrin Inhibits Vascular Smooth Muscle Growth

Micrin was shown to inhibit vascular smooth muscle cell (VSMC) growth in vitro.

Sheep follicular fluid was purified using ion exchange chromatography (see 7a above) and fractions validated for their micrin content using an in vitro assay, where reduction in rat bone marrow stem cell viability was assessed (Scutt, A. and Bartram, P., 1995, *J. Bone and Mineral Research*, 10, 474-489). Four fractions were selected as representative of those showing greatest activity (fractions 62, 66, 68 and 69), all of which showed viability <40% with the most marked effect being seen in fractions 66 and 68 (viability approximately 30%). These fractions were diluted 1:10 in salt-free DMEM/10% FCS such that the final salt concentration was similar to standard DMEM used in the control group.

Rat aortic VSMCs (A10 cell line, American Tissue Culture Collection) were plated at a density of 1×10$^4$ per well on 6-well plates (Triple Red, UK) with 2 ml of DMEM supplemented with 10% FCS. The next day the medium was aspirated and replaced with one of the following:

10% FCS in DMEM

10% FCS in salt free DMEM plus micrin fraction 62, 66, 68 or 69

Each treatment was performed in triplicate. After 72 hours the cells were trypsinised off the dish and centrifuged at 1100 g for 5 minutes. The resulting pellet was resuspended in 6 ml of osmocell (Advanced Medical Supplies, UK) and counted in triplicate using a Coulter counter (Beckman Coulter Z M). Also 25 µl of cells were added to 25 µl of PBS and 50 µl of Trypan blue, as a measure of cell viability. Counts of viable cells were performed using a haemocytometer, with statistical comparisons between the groups using ANOVA and Bonferroni t-test. As shown in Table 4, micrin treatment resulted in inhibition of vascular smooth muscle proliferation in vitro when compared to controls. This effect was significant (p<0.05) in the fractions (66 and 68) showing the most activity in a bone marrow stem cell viability screening assay.

TABLE 4

| Treatment | Mean Cell Number ($10^3$) ± SEM (n = 3) |
|---|---|
| Control (10% FCS) | 144.9 ± 12.9 |
| Fraction 62 | 138.8 ± 4.7 |
| Fraction 66 | 98.5 ± 11.4 (p < 0.05) |
| Fraction 68 | 65.6 ± 8.1 (p < 0.05) |
| Fraction 69 | 116.2 ± 10.5 |

7f. Micrin Inhibits Angiogenesis

Figure 6:
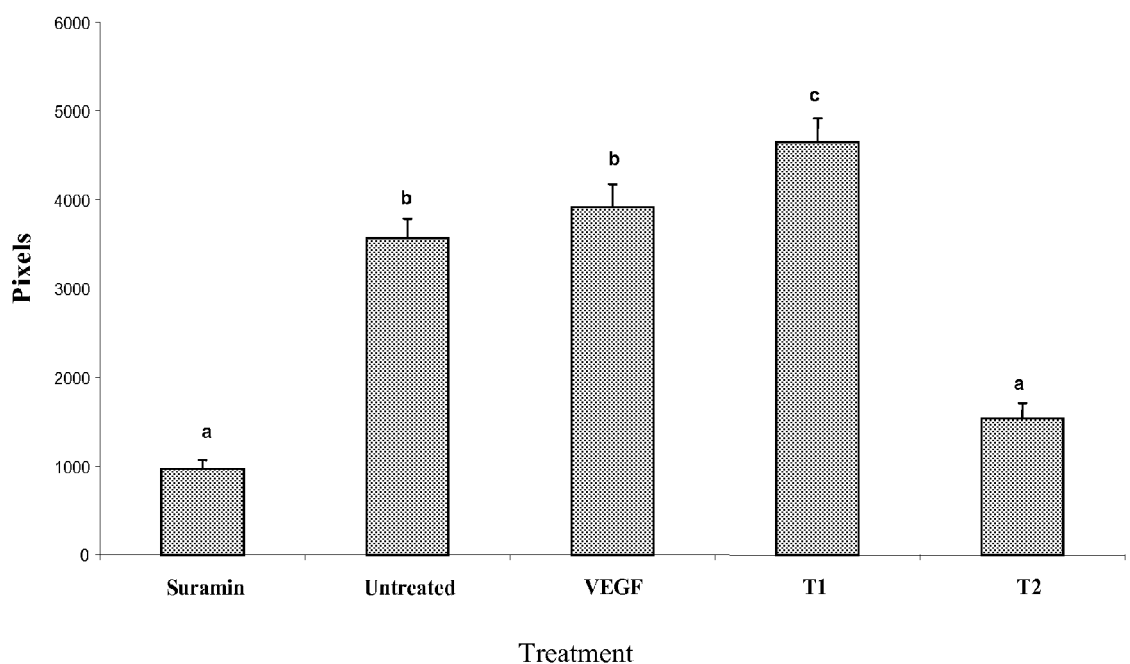
FIG. 6 is a graph showing the inhibition of angiogenesis by micrin (in a sample designated 'T2') in vitro, using a model system of human umbilical vascular endothelial cells (HUVECs)

Micrin was shown to have anti-angiogenic activity in vitro on human umbilical vascular endothelial cells (HUVECs), using a commercially available kit (Human Angiogenesis Kit 'AngioKit', TCS, UK). Micrin and micrin free control samples were produced using the method described in Example 7.a with 120 ml sheep follicular fluid as the source material. These were diluted in AngioKit medium and stored at 4° C. for the duration of the assay. Samples were tested as follows:
1) untreated control—medium alone
2) positive control—medium containing 2 ng/ml VEGF
3) negative control—medium containing 20 µM suramin (a potent inhibitor of angiogenesis)
4) micrin-free control
5) micrin test material Comparison of venule length was conducted using the 'Angiosys' image analysis system developed specifically for the analysis of images produced using the AngioKit. Four images were taken from predetermined positions in the well containing each specimen. The values of average venule length, defined by number of image pixels, are shown in FIG. 6. The results obtained with micrin are marked T2, those with micrin-free control T1. In FIG. 6 groups which are significantly different are marked with different letters (alpha=0.5, one way ANOVA with replicated measures/Duncan's multiple comparison procedure). Suramin treatment caused a statistically significant decrease in HUVEC venule length. A similar significant reduction in venule length was caused by treatment with micrin.

7g. Micrin Peptide Fragment Reduces Pituitary Cell Production of Prolactin and LH Production of prolactin by ovine pituitary cells in vitro was reduced by treatment with the micrin peptide fragment (SEQ ID NO: 9).

Adult ewe pituitaries were collected into phosphate buffered saline (PBS) on ice. The external dura and neurohypophyseal tissue were removed and the remaining tissue was sliced thinly using tweezers and scalpel, and minced using crossed scalpel blades (<1 mm pieces). The mince was washed in 0.1% bovine serum albumen (BSA)/PBS. The tissue was allowed to settle and the liquid aspirated. The washing, settling and aspiration were repeated.

A standard cell dispersion was conducted by adding the tissue to a filtered solution of collagenase in BSA/PBS (0.02-0.03 g in 10 ml) plus Dnase, hyaluronidase, pancreatin and trypsin inhibitor and incubating in a shaking waterbath at 37° C. for 25 minutes. The resultant suspension was titurated with a pipette and returned to the shaking waterbath for 5 minutes. The suspension was titurated again and filtered through a mesh, washing with BSA/PBS. The suspension was added to a 50 ml centrifuge tube and spun at 1500 rpm for 5 minutes. The supernatant was removed and the cell pellet resuspended in 50 ml BSA/PBS.

A sample of the cell suspension (50 µl) was mixed 1:1 with trypan blue in a microcentrifuge tube and viable cells were counted on a haemocytometer, to give viable cell concentration.

The cell suspension was recentrifuged and resuspended in 3-5 ml of M199. Approximately $5 \times 10^5$ viable cells were plated into multiwell plates containing 1 ml of M199 with FCS. These were cultured for 3 days.

Two experiments were conducted, as follows:

EXPERIMENT 1

Sets of 3-4 precultured wells were treated with either saline vehicle or the micrin peptide fragment (SEQ ID NO: 9) at a dose of 1 ng/well in M199 (no serum). After 24 hours the cells were harvested. The media from each were subjected to a radioimmunoassay (RIA) for prolactin using standard methods. In the medium from control treated cells the prolactin level was 92.2±13.9 ng/ml (Mean±SEM n=3). Micrin treatment resulted in lower prolactin levels in the medium: 67.1±12.6 ng/ml (n=4).

EXPERIMENT 2

Sets of 4 precultured wells were treated with either saline vehicle or the micrin peptide fragment (SEQ ID NO: 9) at a dose of 1 µg/ml in M199 (no serum). These were incubated for 2 hours and the medium harvested and assayed for prolactin using a standard RIA assay. In the medium from control treated cells the prolactin levels were 8.30±1.16 ng/ml (which was lower than in Experiment 1 because of the reduced culture time). Prolactin levels in medium from the micrin peptide fragment treated cells were significantly lower at 5.18±1.52 ng/ml (p<0.05 Student's one-tailed t-test).

In both experiments, treatment with the micrin peptide fragment resulted in a reduction in prolactin secretion by ovine pituitary cells in vitro.

It has also been found that the micrin peptide fragment of SEQ ID NO: 9 affects the secretion of luteinising hormone (LH) by ovine pituitary cells in vitro, when a similar experimental procedure is used to that outlined above for prolactin, using the 24 h exposure of Experiment 1. When the cells are provided with GnRH, GHRH and TRH, there is a reduction in LH production. On the other hand, when these hypothalamic regulators are omitted—which is less representative of the normal in vivo situation but representative of pathological hypothalamic insuffiency—the effect of the micrin peptide fragment is to increase the secretion of LH. Both effects are dependent on dose across the range used, 0.1-10 µg/L, and are statistically significant. Comparison was with a control peptide having the same amino acids in a randomly scrambled sequence (data not shown)

7h. Micrin Peptide Fragment Suppresses the Effect of IGF1

The effect of micrin in suppressing compensatory renal growth was described above in section 7b. This growth process is itself related to IGF1 (insulin-like growth factor 1), so similar effects may be expected with other in vitro and in vitro processes that are affected by IGF1.

Experiments were conducted to assess the effects of a range of doses of the micrin peptide fragment with 20 amino acids (SEQ ID NO: 19) on the IGF1-stimulated growth of MCF 7 human breast cancer cells. Cells were plated at $2 \times 10^4$ per well in 2 cm$^2$ wells in Dulbecco's Modified Eagle's Medium containing 10% foetal calf serum, antibiotics and a stabilised substitute for glutamine (Glutamax, InVitrogen, UK). After an overnight culture period, the cells were washed with fresh medium and this was replaced with medium containing IGF1 (50 ng/ml) in the presence and absence of a range of concentrations (between 0.04 and 4000 nmol) of the peptide fragment in triplicate wells, and compared to triplicate wells containing medium only (with no supplementary IGF1) as controls. The cells were incubated for 72 hours in a humidified atmosphere at 37° C. under 5% carbon dioxide/95% air. The medium was discarded, and the cell layer washed with buffered saline before being incubated with trypsin/EDTA to dislodge the cells. The cell suspension was diluted with medium to stop the tryptic action and then transferred to tubes and subjected to centrifugation. The pellet was resuspended in Isoton and samples counted with a Coulter counter. As shown in FIG. 7, which shows the cell numbers after 72 hours as a percentage of those in the controls, the peptide fragment suppresses the effect of IGF1 in a dose-dependent manner: 0.04 nmol of the peptide fragment noticably decreases the cell count (compared to IGF1 alone), while 40 nmol of the peptide fragment reduces the cell count to below that in the controls.

Similar results have also been obtained with the 14-amino acid fragment of SEQ ID NO: 9. The results with the micrin peptide fragment can be somewhat variable however, betokening perhaps the need for the full micrin molecule for a fully reliable effect.

7i. Micrin Peptide Fragment Boosts Nematode Fecundity In Vivo and Reduces Stem Cell Proliferation In Vitro The studies here examined the two aspect of the hypothesized micrin puberty signal directing organisms to start reproducing and cease growing.

It has been found using the nematode *Caenorhabditis elegans* that the micrin peptide fragment of SEQ ID NO: 9, when administered each day to the worms' aqueous medium at a concentration of 1 μM (the worms being transferred to fresh medium each day), increases by >40% the fecundity (number of offspring) of adult nematode worms over their lifespan—and that the lifetime itself was increased by about a fifth. A fluorescently tagged version of the micrin peptide fragment appeared to accumulate preferentially in genital tissue. (For methodology see Davies, K. G & Hart, J. E, *Nematology*, 10, 103-112, 2008).

The first six amino acids of the micrin peptide fragment of SEQ ID NO: 9 are MKPLTG (SEQ ID NO: 26). These have been synthesized as a 6 mer. This has been found to increase fecundity 50%, using the nematode worm assay protocol above, without altering lifespan. Thus the fecundity-enhancing effect is retained even if 8 of the 14 amino acids are removed, potentially identifying an active motif. To optimise this 6 mer further, amino acid substitutions have been made, while retaining the proline at position 3. LQPAHV (SEQ ID NO. 27) at the 1 μM dose level each day was found to increase fecundity by 71% and also significantly to prolong lifespan, while IEPVFT (SEQ ID NO. 28) increased fecundity by 79%, without having a significant effect on lifespan. Adding for example KLKMNGKN (SEQ ID NO: 29) to the N-terminus of IEPVFT (SEQ ID NO: 30) turns a fecundity agent into an anti-fecundity agent (Davies, K. G & Hart, J. E, *Nematology*, 10, 103-112, 2008).

To investigate the stop growing aspect of the hypothesized micrin puberty signal, the proline-containing 6 mers have been administered to human bone marrow stem cells in an in vitro assay (see 6a), at a concentration in the medium of 1 μM. In ascending order of anti-proliferative activity the 6 mers were IEPVFT (SEQ ID NO: 30)<MKPLTG (SEQ ID NO. 26)<LEPVMT (SEQ ID NO: 31)<LQPAHV (SEQ ID NO: 27), with the last-mentioned 6 mer reducing cell numbers by about 32% over the 24 h duration of the study.

In a separate in vitro study involving human dental pulp cells at a cell seeding density of $5.0 \times 10^3$ cells/ml, MKPLTG (SEQ ID NO: 26) was minimally anti-proliferative (Cyquant, Invitrogen) at 5 μM in the cell medium, the peptide of SEQ ID NO:1 was more so and the C-terminus KVKEFNNI (SEQ ID NO: 21) most anti-proliferative of all, the last-mentioned reducing cell numbers by about 17% over 7 days. Molecular modelling in silico indicates that FNNI (SEQ ID NO: 4) is probably the biologically active motif.

The experimental observations in 7g, involving ovine pituitary cell cultures, and 7l, relating to nematode fecundity, suggest that micrin modulates the reproductive axis.

8. Discussion

From the above studies and on the basis of findings disclosed in an earlier document (WO 00/32208), an important role for micrin can be posited in what has been previously described (WO 00/32208) as the 'organotrophic system', the totality of hormonal, neural, mechanical and other influences on tissue and organ size. Within this system micrin is envisaged as operating as the body's 'brake', preventing runaway overgrowth. Micrin may be particularly important during puberty, delivering a 'stop growing and start reproducing' signal to the organism.

There would appear to be two aspects to the braking effect: local inhibition, brought about by micrin produced in neuroendocrine cells throughout the body; and central regulation of the pituitary 'accelerator', via the production of hypothalamic micrin.

Without the intention of being bound by theory, it is thought that micrin seems to exert its effects via multiple mechanisms to inhibit tissue and organ size. These mechanisms include cell shrinkage, inhibition of proliferation, induction of apoptosis and suppression of angiogenesis, and could conjecturally extend to inhibition of lymphangiogenesis and alterations in the extracellular matrix, among other additional mechanisms. Furthermore, different effects of micrins seem to be associated with different parts of the molecule. For example, suppression of IGF1-stimulated proliferation is associated with the part of the molecule in SEQ ID NOs: 9 and 19, while apoptotic activity seems to be associated with another part of the molecule. As a further example, the 14 mer micrin peptide fragment, SEQ ID NO: 9, appears to promote fecundity and prolongation of lifespan in the nematode *C. elegans*, while the first six amino acids of SEQ ID NO: 9 synthesized as a timer appear to promote fecundity alone.

Full length micrin (and physiologically active peptide fragments thereof) appears to be suitable for a range of therapeutic applications, based on its natural actions as a tissue-mass inhibitor. For example, micrin may have utility in the treatment of pituitary adenoma. Reduction in the size of the pituitary and of other organs has been demonstrated in vivo using impure micrin (WO 00/32208). That micrin reduces basal prolactin secretion by pituitary cells, as described herein (see above, 7g), is especially interesting, given the prevalence of prolactinomas.

Tissues and organs appear to have a 'set point' with regard to size. Micrin causes size reduction more readily where the set point is exceeded (for example, in benign prostatic hyperplasia) than where the tissue or organ is at or near its set point. In this sense, exogenous micrin tends to be self-selective for overgrown tissues and organs.

The resistance of normal-sized tissues to micrin is important, for example in considering micrin-induced apoptosis. Micrin administration to animals has been associated with no discernible toxicity: a wave of apoptosis does not pass through the organism. Apoptosis seems confined to a subset of cells in overgrown tissues and organs only.

That micrin does induce apoptosis in vitro, however, as herein described (see above, 7a), implies that cells in culture are abnormal in status. Since tumour cells in vitro are prompted to commit suicide, this suggests that cellular 'knowledge' of abnormality survives neoplastic transformation and that tumour cells do not 'escape' micrin control. Micrin is thus potentially a threat to all tumour cells, primary and secondary.

PC12 tumour cells have been shown to produce micrin, paradoxically given its inhibitory character, and this effect has been used as the basis of a production method of human micrin.

Micrin directs organisms away from growth and towards reproduction. This view is supported by the data on tissue inhibition, taken together with the pituitary findings of 7g and the nematode fecundity findings of 7l. This would support the potential use of micrin-related drugs in infertility and other reproductive disorders, and predicts the non-impairment of the reproductive system when micrin is used therapeutically in non-reproductive applications.

In view of the association of IGF1 with the ageing process, and the effectiveness with which micrin or the peptide fragment of SEQ ID NOs: 9 or 19 can suppress the effect of IGF1 (as shown in section 7h), it can be expected that micrin may retard the ageing process. This is supported by the greater lifespan of nematode worms receiving the micrin peptide fragment, as reported in 7l, than those receiving a scrambled peptide or no treatment. A therapeutic usage can therefore be anticipated for micrin in combating senescence and enhancing lifespan.

Therapeutic interventions can also be anticipated in psychiatric conditions, whether such interventions are based on increasing or decreasing micrin. In immunohistochemical investigations using an antibody to the micrin peptide fragment, SEQ ID NO: 9, sections of rat brain were used. Staining was confined exquisitely to the pyramidal cells of cerebral cortex layer 5, supporting a view that micrin is neuromodulatary. These are the neurons involved in cognition and learning and are among those affected in Alzheimer's.

The invention claimed is:

1. An isolated polypeptide that comprises an amino acid sequence at the N-terminus end that is a 6-mer motif selected from LQPAHV (SEQ ID NO:27), LEPVMT (SEQ ID NO:31), and IEPVFT (SEQ ID NO:30).

2. An isolated polypeptide according to claim 1 that is IEPVFT (SEQ ID NO:30).

3. An isolated polypeptide according to claim 1 that is LQPAHV (SEQ ID NO:27).

4. An isolated polypeptide that is the 6-mer amino acid sequence MKPLTG (SEQ ID NO:26).

5. An isolated polypeptide that comprises an amino acid sequence at the N-terminus end according to Formula (III):

$$1\text{-}2\text{-}P\text{-}3\text{-}T\text{-}5\text{-}6\text{-}7\text{-}K\text{-}8\text{-}F\text{-}N\text{-}9\text{-}10 \quad \text{Formula (III)}$$

wherein:
1 is independently selected from amino acids S, D, L, I and M;
2 is independently selected from amino acids S, Q, E, K, L and T;
3 is independently selected from amino acids A, V, L, F, G and E;
5 is independently selected from amino acids V, T, G and Y;
6 is independently selected from amino acids K and W;
7 is independently selected from amino acids V and I;
8 is independently selected from amino acids E and K;
9 is independently selected from amino acids N and A;
10 is independently selected from amino acids I and V and P is a proline residue.

6. A polypeptide according to claim 5 that is:

MKPLTGKVKEFNNI.    SEQ ID NO. 30

7. An isolated polypeptide according to claim 1 that is LEPVMT (SEQ ID NO:31).

* * * * *

SEQUENCE LISTING

```
<160> NUMBER OF SEQ ID NOS: 34

<210> SEQ ID NO 1
<211> LENGTH: 14
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (1)..(1)
<223> OTHER INFORMATION: Xaa is independently selected from Ser, Asp and
      Met

<400> SEQUENCE: 1

Xaa Lys Pro Leu Thr Gly Lys Val Lys Glu Phe Asn Asn Ile
1               5                   10

<210> SEQ ID NO 2
<211> LENGTH: 20
<212> TYPE: PRT
<213> ORGANISM: Artificial sequence
<220> FEATURE:
<223> OTHER INFORMATION: Synthetic sequence
<220> FEATURE:
<221> NAME/KEY: VARIANT
<222> LOCATION: (1)..(1)
<223> OTHER INFORMATION: Xaa is either Ser, Asp or Met
<220> FEATURE:
<221> NAME/KEY: VARIANT
<222> LOCATION: (18)..(18)
<223> OTHER INFORMATION: Xaa is any amino acid residue

<400> SEQUENCE: 2

Xaa Lys Pro Leu Thr Gly Lys Val Lys Glu Phe Asn Asn Ile Lys Gly
1               5                   10                  15

Phe Xaa Val Ile
            20

<210> SEQ ID NO 3
<211> LENGTH: 14
<212> TYPE: PRT
<213> ORGANISM: Artificial sequence
<220> FEATURE:
<223> OTHER INFORMATION: Synthetic sequence: Formula (III) of
```

```
        PCT/GB2009/050021
<220> FEATURE:
<221> NAME/KEY: VARIANT
<222> LOCATION: (1)..(1)
<223> OTHER INFORMATION: Xaa is independently selected from Ser, Asp,
      Leu, Ile, and Met
<220> FEATURE:
<221> NAME/KEY: VARIANT
<222> LOCATION: (2)..(2)
<223> OTHER INFORMATION: Xaa is independently selected from Ser, Gln,
      Glu, Lys, Leu and Thr
<220> FEATURE:
<221> NAME/KEY: VARIANT
<222> LOCATION: (4)..(4)
<223> OTHER INFORMATION: Xaa is independently selected from Ala, Val,
      Leu, Phe, Gly and Glu
<220> FEATURE:
<221> NAME/KEY: VARIANT
<222> LOCATION: (6)..(6)
<223> OTHER INFORMATION: Xaa is independently selected from Val, Thr,
      Gly and Tyr
<220> FEATURE:
<221> NAME/KEY: VARIANT
<222> LOCATION: (7)..(7)
<223> OTHER INFORMATION: Xaa is independently selected from Lys and Trp
<220> FEATURE:
<221> NAME/KEY: VARIANT
<222> LOCATION: (8)..(8)
<223> OTHER INFORMATION: Xaa is independently selected from Val and Ile
<220> FEATURE:
<221> NAME/KEY: VARIANT
<222> LOCATION: (10)..(10)
<223> OTHER INFORMATION: Xaa is independently selected from Glu and Lys
<220> FEATURE:
<221> NAME/KEY: VARIANT
<222> LOCATION: (13)..(13)
<223> OTHER INFORMATION: Xaa is independently selected from Asn and Ala
<220> FEATURE:
<221> NAME/KEY: VARIANT
<222> LOCATION: (14)..(14)
<223> OTHER INFORMATION: Xaa is independently selected from Ile and Val

<400> SEQUENCE: 3

Xaa Xaa Pro Xaa Thr Xaa Xaa Xaa Lys Xaa Phe Asn Xaa Xaa
1               5                   10

<210> SEQ ID NO 4
<211> LENGTH: 4
<212> TYPE: PRT
<213> ORGANISM: Artificial sequence
<220> FEATURE:
<223> OTHER INFORMATION: Synthetic sequence

<400> SEQUENCE: 4

Phe Asn Asn Ile
1

<210> SEQ ID NO 5
<211> LENGTH: 4
<212> TYPE: PRT
<213> ORGANISM: Artificial sequence
<220> FEATURE:
<223> OTHER INFORMATION: Synthetic sequence

<400> SEQUENCE: 5

Phe Asn Asn Gly
1

<210> SEQ ID NO 6
<211> LENGTH: 6
<212> TYPE: PRT
<213> ORGANISM: Artificial sequence
<220> FEATURE:
<223> OTHER INFORMATION: Synthetic sequence
```

```
<220> FEATURE:
<221> NAME/KEY: VARIANT
<222> LOCATION: (4)..(4)
<223> OTHER INFORMATION: Xaa is any amino acid residue

<400> SEQUENCE: 6

Lys Gly Phe Xaa Val Ile
1               5

<210> SEQ ID NO 7
<211> LENGTH: 14
<212> TYPE: PRT
<213> ORGANISM: Artificial sequence
<220> FEATURE:
<223> OTHER INFORMATION: Synthetic sequence

<400> SEQUENCE: 7

Ser Lys Pro Leu Thr Gly Lys Val Lys Glu Phe Asn Asn Ile
1               5                   10

<210> SEQ ID NO 8
<211> LENGTH: 14
<212> TYPE: PRT
<213> ORGANISM: Artificial sequence
<220> FEATURE:
<223> OTHER INFORMATION: Synthetic sequence

<400> SEQUENCE: 8

Asp Lys Pro Leu Thr Gly Lys Val Lys Glu Phe Asn Asn Ile
1               5                   10

<210> SEQ ID NO 9
<211> LENGTH: 14
<212> TYPE: PRT
<213> ORGANISM: Artificial sequence
<220> FEATURE:
<223> OTHER INFORMATION: Synthetic sequence

<400> SEQUENCE: 9

Met Lys Pro Leu Thr Gly Lys Val Lys Glu Phe Asn Asn Ile
1               5                   10

<210> SEQ ID NO 10
<211> LENGTH: 20
<212> TYPE: DNA
<213> ORGANISM: Artificial sequence
<220> FEATURE:
<223> OTHER INFORMATION: Synthetic sequence: Degenerate 5-prime primer
<220> FEATURE:
<221> NAME/KEY: misc_feature
<222> LOCATION: (3)..(3)
<223> OTHER INFORMATION: n is a, g, c, or t

<400> SEQUENCE: 10
gtnaargart tyaayaayat                                                   20

<210> SEQ ID NO 11
<211> LENGTH: 7
<212> TYPE: PRT
<213> ORGANISM: Artificial sequence
<220> FEATURE:
<223> OTHER INFORMATION: Synthetic sequence

<400> SEQUENCE: 11

Val Lys Glu Phe Asn Asn Ile
1               5

<210> SEQ ID NO 12
```

-continued

```
<211> LENGTH: 25
<212> TYPE: DNA
<213> ORGANISM: Artificial sequence
<220> FEATURE:
<223> OTHER INFORMATION: Synthetic sequence: Primer
<220> FEATURE:
<221> NAME/KEY: misc_feature
<222> LOCATION: (8)..(8)
<223> OTHER INFORMATION: n is a, g, c, or t

<400> SEQUENCE: 12
ccgcggtnaa rgarttyaay aayat                                              25

<210> SEQ ID NO 13
<211> LENGTH: 24
<212> TYPE: DNA
<213> ORGANISM: Artificial sequence
<220> FEATURE:
<223> OTHER INFORMATION: Synthetic sequence: Primer
<220> FEATURE:
<221> NAME/KEY: misc_feature
<222> LOCATION: 3, 9, 12
<223> OTHER INFORMATION: n is a, g, c, or t

<400> SEQUENCE: 13
ggnaargtna cngayttyaa yaay                                               24

<210> SEQ ID NO 14
<211> LENGTH: 7
<212> TYPE: PRT
<213> ORGANISM: Artificial sequence
<220> FEATURE:
<223> OTHER INFORMATION: Synthetic sequence

<400> SEQUENCE: 14

Lys Val Thr Asp Phe Asn Asn
1               5

<210> SEQ ID NO 15
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 15
gcggccgctt tttttttttt tttttttt                                           28

<210> SEQ ID NO 16
<211> LENGTH: 879
<212> TYPE: DNA
<213> ORGANISM: Rattus sp.

<400> SEQUENCE: 16
ggcacctacc ttgtcagctt cactctgttc tgggagggcc aggtctccct gtctatcctg        60
ctcatgcacc ccagtgaagg ggtgtcagct ctctggagag caaggaacca gggttacgac       120
agaatcatct tctcaggcca ttttgtcagt ggcgcttcca ggtccacacc gattgtgccc       180
tggttctaaa ttcaagtgtc gagctatgtc agtatctgga tgcccaggac caagaagctt       240
tctactgtgt gaagcctcca aatgtgccct gtgcggccat cacccacatg cattccaaga       300
acaaggacat ttcttatctt agccagcagg aaaggagcct ctttgaaagg tcaaatatag       360
ctgtggagat tatgggaaaa tccaacgtga ttagtgtctc caaatgcaac aaagccgtcc       420
cggtgaagaa gaaatgcaag tttgggatgg catctgcaat ccctactggg catgtctgga       480 aaacacgtg gaatccggcc tcctgcagtc tggctccaat caaaatgaaa gactgcctga       540
```

-continued

```
gaggaaaact cgtccatcta atgggtgatt ccacaatgcg ccagtggatg gagtacttca    600
aaagcaaaat caacacgctg aggccggtgg acctccacga gactggaagg ctgcagcacc    660
aacttgccgt ggacttggat gagaaaatca acatccagtg gcagaaacat ggcttccctc    720
taatcgggtc attggtgtac tctgtcaaag agatagagaa cactgcacgg ataattgaca    780
gaatcggagg agagaaaaac acagtcattg tcttttctct gggccagcat ttcagacctt    840
ttcccattga tgttttatc cgaagggccc tcagtgttc                            879
```

<210> SEQ ID NO 17
<211> LENGTH: 293
<212> TYPE: PRT
<213> ORGANISM: Rattus sp.

<400> SEQUENCE: 17

```
Gly Thr Tyr Leu Val Ser Phe Thr Leu Phe Trp Glu Gly Gln Val Ser
1               5                   10                  15

Leu Ser Ile Leu Leu Met His Pro Ser Glu Gly Val Ser Ala Leu Trp
            20                  25                  30

Arg Ala Arg Asn Gln Gly Tyr Asp Arg Ile Ile Phe Ser Gly His Phe
        35                  40                  45

Val Ser Gly Ala Ser Gln Val His Thr Asp Cys Ala Leu Val Leu Asn
    50                  55                  60

Ser Ser Val Glu Leu Cys Gln Tyr Leu Asp Ala Gln Asp Gln Glu Ala
65                  70                  75                  80

Phe Tyr Cys Val Lys Pro Pro Asn Val Pro Cys Ala Ala Ile Thr His
                85                  90                  95

Met His Ser Lys Asn Lys Asp Ile Ser Tyr Leu Ser Gln Gln Glu Arg
            100                 105                 110

Ser Leu Phe Glu Arg Ser Asn Ile Ala Val Glu Ile Met Gly Lys Ser
        115                 120                 125

Asn Val Ile Ser Val Ser Lys Cys Asn Lys Ala Val Pro Val Lys Lys
    130                 135                 140

Lys Cys Lys Phe Gly Met Ala Ser Ala Ile Pro Thr Gly His Val Trp
145                 150                 155                 160

Lys Asn Thr Trp Asn Pro Ala Ser Cys Ser Leu Ala Pro Ile Lys Met
                165                 170                 175

Lys Asp Cys Leu Arg Gly Lys Leu Val His Leu Met Gly Asp Ser Thr
            180                 185                 190

Met Arg Gln Trp Met Glu Tyr Phe Lys Ser Lys Ile Asn Thr Leu Arg
        195                 200                 205

Pro Val Asp Leu His Glu Thr Gly Arg Leu Gln His Gln Leu Ala Val
    210                 215                 220

Asp Leu Asp Glu Lys Ile Asn Ile Gln Trp Gln Lys His Gly Phe Pro
225                 230                 235                 240

Leu Ile Gly Ser Leu Val Tyr Ser Val Lys Glu Ile Glu Asn Thr Ala
                245                 250                 255

Arg Ile Ile Asp Arg Ile Gly Gly Glu Lys Asn Thr Val Ile Val Phe
            260                 265                 270

Ser Leu Gly Gln His Phe Arg Pro Phe Pro Ile Asp Val Phe Ile Arg
        275                 280                 285

Arg Ala Leu Ser Val
    290
```

<210> SEQ ID NO 18

```
<211> LENGTH: 15
<212> TYPE: PRT
<213> ORGANISM: Artificial sequence
<220> FEATURE:
<223> OTHER INFORMATION: Synthetic sequence

<400> SEQUENCE: 18

Cys Met Lys Pro Leu Thr Gly Lys Val Lys Glu Phe Asn Asn Ile
1               5                   10                  15

<210> SEQ ID NO 19
<211> LENGTH: 20
<212> TYPE: PRT
<213> ORGANISM: Artificial sequence
<220> FEATURE:
<223> OTHER INFORMATION: Synthetic sequence

<400> SEQUENCE: 19

Met Lys Pro Leu Thr Gly Lys Val Lys Glu Phe Asn Asn Ile Lys Gly
1               5                   10                  15

Phe Gly Val Ile
            20

<210> SEQ ID NO 20
<211> LENGTH: 21
<212> TYPE: PRT
<213> ORGANISM: Artificial sequence
<220> FEATURE:
<223> OTHER INFORMATION: Synthetic sequence

<400> SEQUENCE: 20

Cys Met Lys Pro Leu Thr Gly Lys Val Lys Glu Phe Asn Asn Ile Lys
1               5                   10                  15

Gly Phe Gly Val Ile
            20

<210> SEQ ID NO 21
<211> LENGTH: 8
<212> TYPE: PRT
<213> ORGANISM: Artificial sequence
<220> FEATURE:
<223> OTHER INFORMATION: Synthetic sequence

<400> SEQUENCE: 21

Lys Val Lys Glu Phe Asn Asn Ile
1               5

<210> SEQ ID NO 22
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 22
atgggctcct tctccatcac                                          20

<210> SEQ ID NO 23
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 23
tcttcggtac cgggaagct                                           19
```

```
<210> SEQ ID NO 24
<211> LENGTH: 17
<212> TYPE: DNA
<213> ORGANISM: Artificial sequence
<220> FEATURE:
<223> OTHER INFORMATION: Synthetic sequence: Primer

<400> SEQUENCE: 24
ccttcattga cctcaac                                                 17

<210> SEQ ID NO 25
<211> LENGTH: 17
<212> TYPE: DNA
<213> ORGANISM: Artificial sequence
<220> FEATURE:
<223> OTHER INFORMATION: Synthetic sequence: Primer

<400> SEQUENCE: 25
agttgtcatg gatgacc                                                 17

<210> SEQ ID NO 26
<211> LENGTH: 6
<212> TYPE: PRT
<213> ORGANISM: Artificial sequence
<220> FEATURE:
<223> OTHER INFORMATION: Synthetic sequence

<400> SEQUENCE: 26

Met Lys Pro Leu Thr Gly
1               5

<210> SEQ ID NO 27
<211> LENGTH: 6
<212> TYPE: PRT
<213> ORGANISM: Artificial sequence
<220> FEATURE:
<223> OTHER INFORMATION: Synthetic sequence

<400> SEQUENCE: 27

Leu Gln Pro Ala His Val
1               5

<210> SEQ ID NO 28
<211> LENGTH: 6
<212> TYPE: PRT
<213> ORGANISM: Artificial sequence
<220> FEATURE:
<223> OTHER INFORMATION: Synthetic sequence

<400> SEQUENCE: 28

Ile Glu Pro Val Phe Thr
1               5

<210> SEQ ID NO 29
<211> LENGTH: 8
<212> TYPE: PRT
<213> ORGANISM: Artificial sequence
<220> FEATURE:
<223> OTHER INFORMATION: Synthetic sequence

<400> SEQUENCE: 29

Lys Leu Lys Met Asn Gly Lys Asn
1               5

<210> SEQ ID NO 30
<211> LENGTH: 6
<212> TYPE: PRT
```

```
<213> ORGANISM: Artificial sequence
<220> FEATURE:
<223> OTHER INFORMATION: Synthetic sequence

<400> SEQUENCE: 30

Ile Glu Pro Val Phe Thr
1               5

<210> SEQ ID NO 31
<211> LENGTH: 6
<212> TYPE: PRT
<213> ORGANISM: Artificial sequence
<220> FEATURE:
<223> OTHER INFORMATION: Synthetic sequence

<400> SEQUENCE: 31

Leu Glu Pro Val Met Thr
1               5

<210> SEQ ID NO 32
<211> LENGTH: 1659
<212> TYPE: DNA
<213> ORGANISM: Rattus sp.
<220> FEATURE:
<221> NAME/KEY: CDS
<222> LOCATION: (1)..(1629)

<400> SEQUENCE: 32 atg aaa atg atg gcc agt cgt aag tca ctg tgg gtg ctg ctg ttt ata      48
Met Lys Met Met Ala Ser Arg Lys Ser Leu Trp Val Leu Leu Phe Ile
1               5                   10                  15 gtg atc ttc tgg atc tct ttt acc gtt ttc aga aac ccc gtg aag cta      96
Val Ile Phe Trp Ile Ser Phe Thr Val Phe Arg Asn Pro Val Lys Leu
                20                  25                  30 tgg gct gtg ttt aag ctg cct gca tcc ttc aat caa tgg gac ttg atc     144
Trp Ala Val Phe Lys Leu Pro Ala Ser Phe Asn Gln Trp Asp Leu Ile
            35                  40                  45 atg aaa tcc tca tgc cct aaa gtg cct ctc aat cca tca gtt tca cca     192
Met Lys Ser Ser Cys Pro Lys Val Pro Leu Asn Pro Ser Val Ser Pro
        50                  55                  60 aca gag aca gag ctg aga atc agg gag atc cta gag aaa cta aac aaa     240
Thr Glu Thr Glu Leu Arg Ile Arg Glu Ile Leu Glu Lys Leu Asn Lys
65                  70                  75                  80 cag atc cct ccc aga ccc ttc gcc cac ctc aac aac acc aca agt gct     288
Gln Ile Pro Pro Arg Pro Phe Ala His Leu Asn Asn Thr Thr Ser Ala
                85                  90                  95 aca cac agc ata gcc acc atc ctc aac cct caa gat aca tac tgt gta     336
Thr His Ser Ile Ala Thr Ile Leu Asn Pro Gln Asp Thr Tyr Cys Val
            100                 105                 110 ggg gac cag ctg gac atc ctg gta gag gct aga gac cac cta aga aac     384
Gly Asp Gln Leu Asp Ile Leu Val Glu Ala Arg Asp His Leu Arg Asn
        115                 120                 125 agg aaa ggg tat ggt ggg gac ttc ctg agg gcc agg atg tct tct cca     432
Arg Lys Gly Tyr Gly Gly Asp Phe Leu Arg Ala Arg Met Ser Ser Pro
    130                 135                 140 gcc ctg aag gca ggc gct tct gga aaa gtg aca gac ttc aac aat ggc     480
Ala Leu Lys Ala Gly Ala Ser Gly Lys Val Thr Asp Phe Asn Asn Gly
145                 150                 155                 160 acc tac ctt gtc agc ttc act ctg ttc tgg gag ggc cag gtc tcc ctg     528
Thr Tyr Leu Val Ser Phe Thr Leu Phe Trp Glu Gly Gln Val Ser Leu
                165                 170                 175 tct atc ctg ctc atg cac ccc agt gaa ggg gtg tca gct ctc tgg aga     576
Ser Ile Leu Leu Met His Pro Ser Glu Gly Val Ser Ala Leu Trp Arg
            180                 185                 190
```

```
                                                           -continued gca agg aac cag ggt tac gac aga atc atc ttc tca ggc cat ttt gtc        624
Ala Arg Asn Gln Gly Tyr Asp Arg Ile Ile Phe Ser Gly His Phe Val
        195                 200                 205 agt ggc gct tct cag gtc cac acc gat tgt gcc ctg gtt cta aat tca        672
Ser Gly Ala Ser Gln Val His Thr Asp Cys Ala Leu Val Leu Asn Ser
    210                 215                 220 agt gtc gag cta tgt cag tat ctg gat gcc cag gac caa gaa gct ttc        720
Ser Val Glu Leu Cys Gln Tyr Leu Asp Ala Gln Asp Gln Glu Ala Phe
225                 230                 235                 240 tac tgt gtg aag cct cca aat gtg ccc tgt gcg gcc atc acc cac atg        768
Tyr Cys Val Lys Pro Pro Asn Val Pro Cys Ala Ala Ile Thr His Met
                245                 250                 255 cat tcc aag aac aag gac att tct tat ctt agc cag cag gaa agg agc        816
His Ser Lys Asn Lys Asp Ile Ser Tyr Leu Ser Gln Gln Glu Arg Ser
            260                 265                 270 ctc ttt gaa agg tca aat ata gct gtg gag att atg gga aaa tcc aac        864
Leu Phe Glu Arg Ser Asn Ile Ala Val Glu Ile Met Gly Lys Ser Asn
        275                 280                 285 gtg att agt gtc tcc aaa tgc aac aaa gcc gtc ccg gtg aag aag aaa        912
Val Ile Ser Val Ser Lys Cys Asn Lys Ala Val Pro Val Lys Lys Lys
    290                 295                 300 tgc aag ttt ggg atg gca tct gca atc cct act ggg cat gtc tgg aaa        960
Cys Lys Phe Gly Met Ala Ser Ala Ile Pro Thr Gly His Val Trp Lys
305                 310                 315                 320 aac acg tgg aat ccg gcc tcc tgc agt ctg gct cca atc aaa atg aaa       1008
Asn Thr Trp Asn Pro Ala Ser Cys Ser Leu Ala Pro Ile Lys Met Lys
                325                 330                 335 gac tgc ctg aga gga aaa ctc gtc cat cta atg ggt gat tcc aca atg       1056
Asp Cys Leu Arg Gly Lys Leu Val His Leu Met Gly Asp Ser Thr Met
            340                 345                 350 cgc cag tgg atg gag tac ttc aaa agc aaa atc aac acg ctg agg ccg       1104
Arg Gln Trp Met Glu Tyr Phe Lys Ser Lys Ile Asn Thr Leu Arg Pro
        355                 360                 365 gtg gac ctc cac gag act gga agg ctg cag cac caa ctt gcc gtg gac       1152
Val Asp Leu His Glu Thr Gly Arg Leu Gln His Gln Leu Ala Val Asp
    370                 375                 380 ttg gat gag aaa atc aac atc cag tgg cag aaa cat ggc ttc cct cta       1200
Leu Asp Glu Lys Ile Asn Ile Gln Trp Gln Lys His Gly Phe Pro Leu
385                 390                 395                 400 atc ggg tca ttg gtg tac tct gtc aaa gag ata gag aac act gca cgg       1248
Ile Gly Ser Leu Val Tyr Ser Val Lys Glu Ile Glu Asn Thr Ala Arg
                405                 410                 415 ata att gac aga atc gga gga gag aaa aac aca gtc att gtc ttt tct       1296
Ile Ile Asp Arg Ile Gly Gly Glu Lys Asn Thr Val Ile Val Phe Ser
            420                 425                 430 ctg ggc cag cat ttc aga cct ttt ccc att gat gtt ttt atc cga agg       1344
Leu Gly Gln His Phe Arg Pro Phe Pro Ile Asp Val Phe Ile Arg Arg
        435                 440                 445 gcc ctc agt gtt cac aga gct ctt cag cgt ctt ctc ctg aga agc ccg       1392
Ala Leu Ser Val His Arg Ala Leu Gln Arg Leu Leu Leu Arg Ser Pro
    450                 455                 460 gac acc ctg gtg gtc ctc aaa aca gaa aac acc agg gag ttg aat aac       1440
Asp Thr Leu Val Val Leu Lys Thr Glu Asn Thr Arg Glu Leu Asn Asn
465                 470                 475                 480 gac atg gag agg ttt agt gac ttc cac ggt tac acc cag tat ctt gcc       1488
Asp Met Glu Arg Phe Ser Asp Phe His Gly Tyr Thr Gln Tyr Leu Ala
                485                 490                 495 tta aag aat atc ttc cag gat ctc cgt gtg ggt gtc att gat gcc tgg       1536
Leu Lys Asn Ile Phe Gln Asp Leu Arg Val Gly Val Ile Asp Ala Trp
            500                 505                 510
```

```
gat atg aca gtt gca tat ggc aca aac gat gtc cat cca cca gag gag    1584
Asp Met Thr Val Ala Tyr Gly Thr Asn Asp Val His Pro Pro Glu Glu
        515                 520                 525 gta gtt aga agt gaa att aat ata ttc tta aac tat att tgc tag        1629
Val Val Arg Ser Glu Ile Asn Ile Phe Leu Asn Tyr Ile Cys
    530                 535                 540 caaacacata actttgaaag tcgctcgttg                                   1659

<210> SEQ ID NO 33
<211> LENGTH: 542
<212> TYPE: PRT
<213> ORGANISM: Rattus sp.

<400> SEQUENCE: 33

Met Lys Met Met Ala Ser Arg Lys Ser Leu Trp Val Leu Leu Phe Ile
1               5                   10                  15

Val Ile Phe Trp Ile Ser Phe Thr Val Phe Arg Asn Pro Val Lys Leu
            20                  25                  30

Trp Ala Val Phe Lys Leu Pro Ala Ser Phe Asn Gln Trp Asp Leu Ile
        35                  40                  45

Met Lys Ser Ser Cys Pro Lys Val Pro Leu Asn Pro Ser Val Ser Pro
    50                  55                  60

Thr Glu Thr Glu Leu Arg Ile Arg Glu Ile Leu Glu Lys Leu Asn Lys
65                  70                  75                  80

Gln Ile Pro Pro Arg Pro Phe Ala His Leu Asn Asn Thr Thr Ser Ala
                85                  90                  95

Thr His Ser Ile Ala Thr Ile Leu Asn Pro Gln Asp Thr Tyr Cys Val
            100                 105                 110

Gly Asp Gln Leu Asp Ile Leu Val Glu Ala Arg Asp His Leu Arg Asn
        115                 120                 125

Arg Lys Gly Tyr Gly Gly Asp Phe Leu Arg Ala Arg Met Ser Ser Pro
    130                 135                 140

Ala Leu Lys Ala Gly Ala Ser Gly Lys Val Thr Asp Phe Asn Asn Gly
145                 150                 155                 160

Thr Tyr Leu Val Ser Phe Thr Leu Phe Trp Glu Gly Gln Val Ser Leu
                165                 170                 175

Ser Ile Leu Leu Met His Pro Ser Glu Gly Val Ser Ala Leu Trp Arg
            180                 185                 190

Ala Arg Asn Gln Gly Tyr Asp Arg Ile Ile Phe Ser Gly His Phe Val
        195                 200                 205

Ser Gly Ala Ser Gln Val His Thr Asp Cys Ala Leu Val Leu Asn Ser
    210                 215                 220

Ser Val Glu Leu Cys Gln Tyr Leu Asp Ala Gln Asp Gln Glu Ala Phe
225                 230                 235                 240

Tyr Cys Val Lys Pro Pro Asn Val Pro Cys Ala Ala Ile Thr His Met
                245                 250                 255

His Ser Lys Asn Lys Asp Ile Ser Tyr Leu Ser Gln Gln Glu Arg Ser
            260                 265                 270

Leu Phe Glu Arg Ser Asn Ile Ala Val Glu Ile Met Gly Lys Ser Asn
        275                 280                 285

Val Ile Ser Val Ser Lys Cys Asn Lys Ala Val Pro Val Lys Lys Lys
    290                 295                 300

Cys Lys Phe Gly Met Ala Ser Ala Ile Pro Thr Gly His Val Trp Lys
305                 310                 315                 320

Asn Thr Trp Asn Pro Ala Ser Cys Ser Leu Ala Pro Ile Lys Met Lys
```

```
                    325                 330                 335
Asp Cys Leu Arg Gly Lys Leu Val His Leu Met Gly Asp Ser Thr Met
                340                 345                 350

Arg Gln Trp Met Glu Tyr Phe Lys Ser Lys Ile Asn Thr Leu Arg Pro
            355                 360                 365

Val Asp Leu His Glu Thr Gly Arg Leu Gln His Gln Leu Ala Val Asp
        370                 375                 380

Leu Asp Glu Lys Ile Asn Ile Gln Trp Gln Lys His Gly Phe Pro Leu
385                 390                 395                 400

Ile Gly Ser Leu Val Tyr Ser Val Lys Glu Ile Glu Asn Thr Ala Arg
                405                 410                 415

Ile Ile Asp Arg Ile Gly Gly Glu Lys Asn Thr Val Ile Val Phe Ser
                420                 425                 430

Leu Gly Gln His Phe Arg Pro Phe Pro Ile Asp Val Phe Ile Arg Arg
                435                 440                 445

Ala Leu Ser Val His Arg Ala Leu Gln Arg Leu Leu Leu Arg Ser Pro
                450                 455                 460

Asp Thr Leu Val Val Leu Lys Thr Glu Asn Thr Arg Glu Leu Asn Asn
465                 470                 475                 480

Asp Met Glu Arg Phe Ser Asp Phe His Gly Tyr Thr Gln Tyr Leu Ala
                485                 490                 495

Leu Lys Asn Ile Phe Gln Asp Leu Arg Val Gly Val Ile Asp Ala Trp
                500                 505                 510

Asp Met Thr Val Ala Tyr Gly Thr Asn Asp Val His Pro Pro Glu Glu
                515                 520                 525

Val Val Arg Ser Glu Ile Asn Ile Phe Leu Asn Tyr Ile Cys
                530                 535                 540

<210> SEQ ID NO 34
<211> LENGTH: 8
<212> TYPE: PRT
<213> ORGANISM: Rattus sp.

<400> SEQUENCE: 34

Gly Lys Val Thr Asp Phe Asn Asn
1               5
```